US010825562B2

(12) United States Patent
Sugiyama et al.

(10) Patent No.: US 10,825,562 B2
(45) Date of Patent: Nov. 3, 2020

(54) MEDICAL IMAGE DISPLAY APPARATUS

(71) Applicant: Canon Medical Systems Corporation, Otawara (JP)

(72) Inventors: Naoki Sugiyama, Otawara (JP); Yosuke Yanagida, Nasushiobara (JP); Daiki Komatsu, Yokohama (JP)

(73) Assignee: Canon Medical Systems Corporation, Otawara (JP)

(*) Notice: Subject to any disclaimer, the term of this patent is extended or adjusted under 35 U.S.C. 154(b) by 150 days.

(21) Appl. No.: 15/874,049

(22) Filed: Jan. 18, 2018

(65) Prior Publication Data
US 2018/0218785 A1 Aug. 2, 2018

(30) Foreign Application Priority Data

Jan. 31, 2017 (JP) ................. 2017-015373

(51) Int. Cl.
*G06K 9/00* (2006.01)
*G16H 30/20* (2018.01)
(Continued)

(52) U.S. Cl.
CPC ............ *G16H 30/20* (2018.01); *A61B 6/032* (2013.01); *A61B 6/037* (2013.01); *A61B 6/4266* (2013.01); *G16H 30/40* (2018.01); *G16H 40/60* (2018.01); *A61B 6/463* (2013.01); *A61B 6/467* (2013.01); *A61B 6/5229* (2013.01); *A61B 8/461* (2013.01); *G06T 2210/41* (2013.01)

(58) Field of Classification Search
CPC ........ G16H 30/20; G16H 30/40; A61B 6/032; A61B 6/037; A61B 6/463; A61B 6/467; A61B 6/5229; A61B 8/461; G06T 2210/41

USPC ......................................... 382/128
See application file for complete search history.

(56) References Cited

U.S. PATENT DOCUMENTS

2005/0041844 A1* 2/2005 Yamanaka ............ G06T 7/0012
382/128
2006/0126909 A1* 6/2006 Marshall ............... G06T 7/0012
382/128
(Continued)

FOREIGN PATENT DOCUMENTS

JP  2008-161640  7/2008
JP  2012-143545  8/2012
JP  2015-173693  10/2015

OTHER PUBLICATIONS

Office Action dated Aug. 25, 2020 in Japanese Application No. 2017-015373 filed Jan. 31, 2017.

*Primary Examiner* — Jonathan S Lee
(74) *Attorney, Agent, or Firm* — Oblon, McClelland, Maier & Neustadt, L.L.P.

(57) ABSTRACT

According to one embodiment, a medical image display apparatus comprising a memory and processing circuitry. The memory configured to store a task management table associating a processing task executed for a medical image with state information representing whether or not the processing task has been executed. The processing circuitry configured to extract, from the task management table, state information that is associated with a processing task for a medical image requested to be displayed, and display, based on the extracted state information, information indicative of whether or not a processing task has been executed for the requested medical image.

11 Claims, 23 Drawing Sheets

(51) Int. Cl.
    *G16H 30/40*     (2018.01)
    *A61B 6/03*     (2006.01)
    *G16H 40/60*     (2018.01)
    *A61B 6/00*     (2006.01)
    *A61B 8/00*     (2006.01)

(56) References Cited

U.S. PATENT DOCUMENTS

| | | | |
|---|---|---|---|
| 2009/0213034 A1* | 8/2009 | Wu | G16H 30/20 345/1.1 |
| 2012/0323605 A1* | 12/2012 | Okuyama | A61B 6/463 705/3 |
| 2017/0303865 A1* | 10/2017 | Kojima | A61B 5/742 |
| 2018/0329609 A1* | 11/2018 | De Swarte | G06F 3/04842 |

* cited by examiner

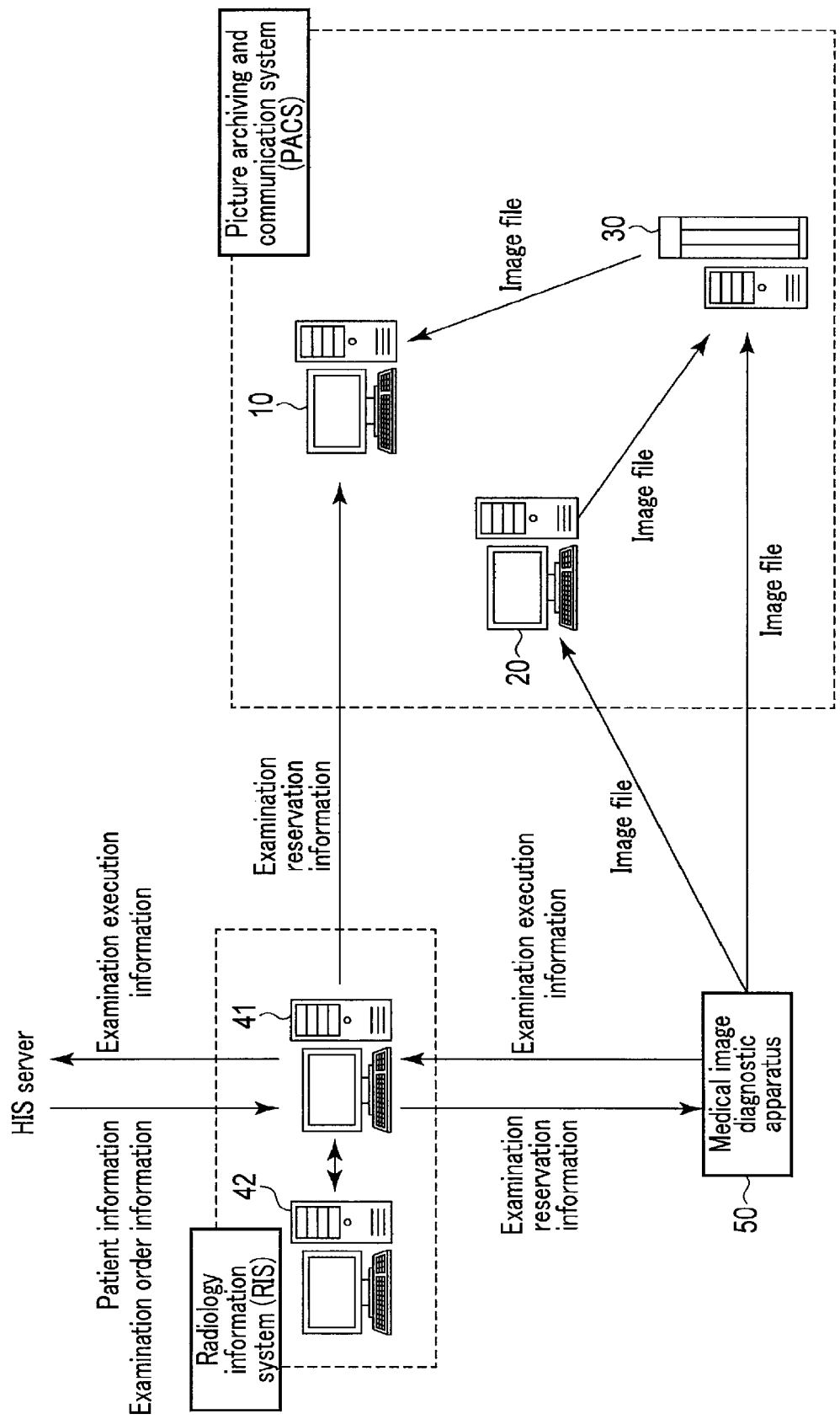
F I G. 1

| Clinical keyword | Processing task |
|---|---|
| CT, large intestine, colonography | Large intestine analysis |
| CT, lung, nodule | Pulmonary nodule analysis |
| CT, liver, tumor | Liver region segmentation analysis |
| CT, atrium, pulmonary artery, arrhythmia | EP planning |
| CT, aortic aneurysm, stent | Stent planning |
| CT | MPR |
| MRI | MPR |
| ... | ... |

F I G. 5

| Oder number | Processing task | State information |
|---|---|---|
| 000001 | Large intestine analysis | Unexecuted |
| 000001 | MPR | Unexecuted |
| ... | ... | ... |
| ... | ... | ... |
| ... | ... | ... |

F I G. 6

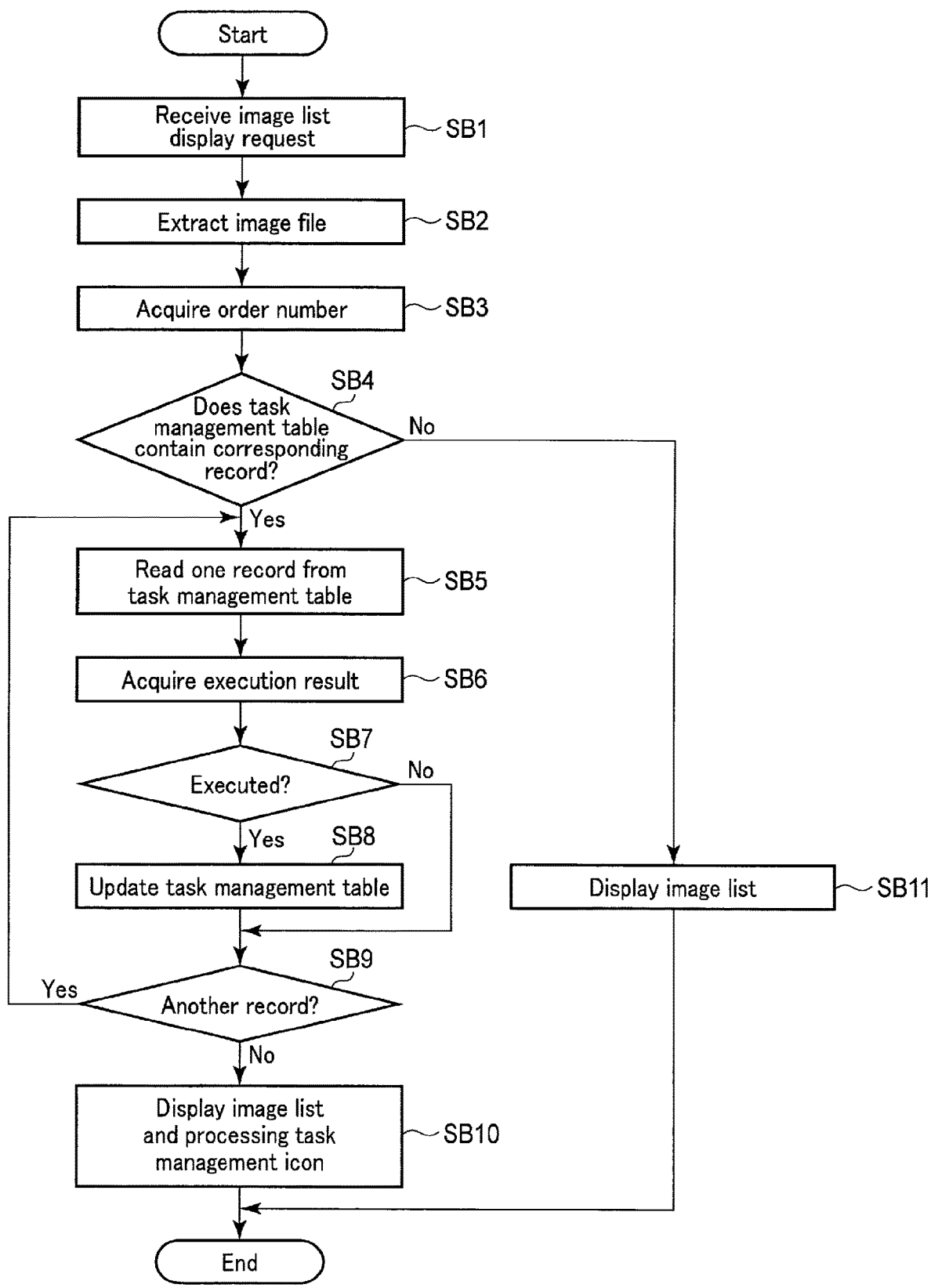
F I G. 7

| Oder number | Processing task | State information |
|---|---|---|
| 000001 | Large intestine analysis | Unexecuted |
| 000001 | MPR | Executed |
| ... | ... | ... |
| ... | ... | ... |
| ... | ... | ... |

F I G. 9

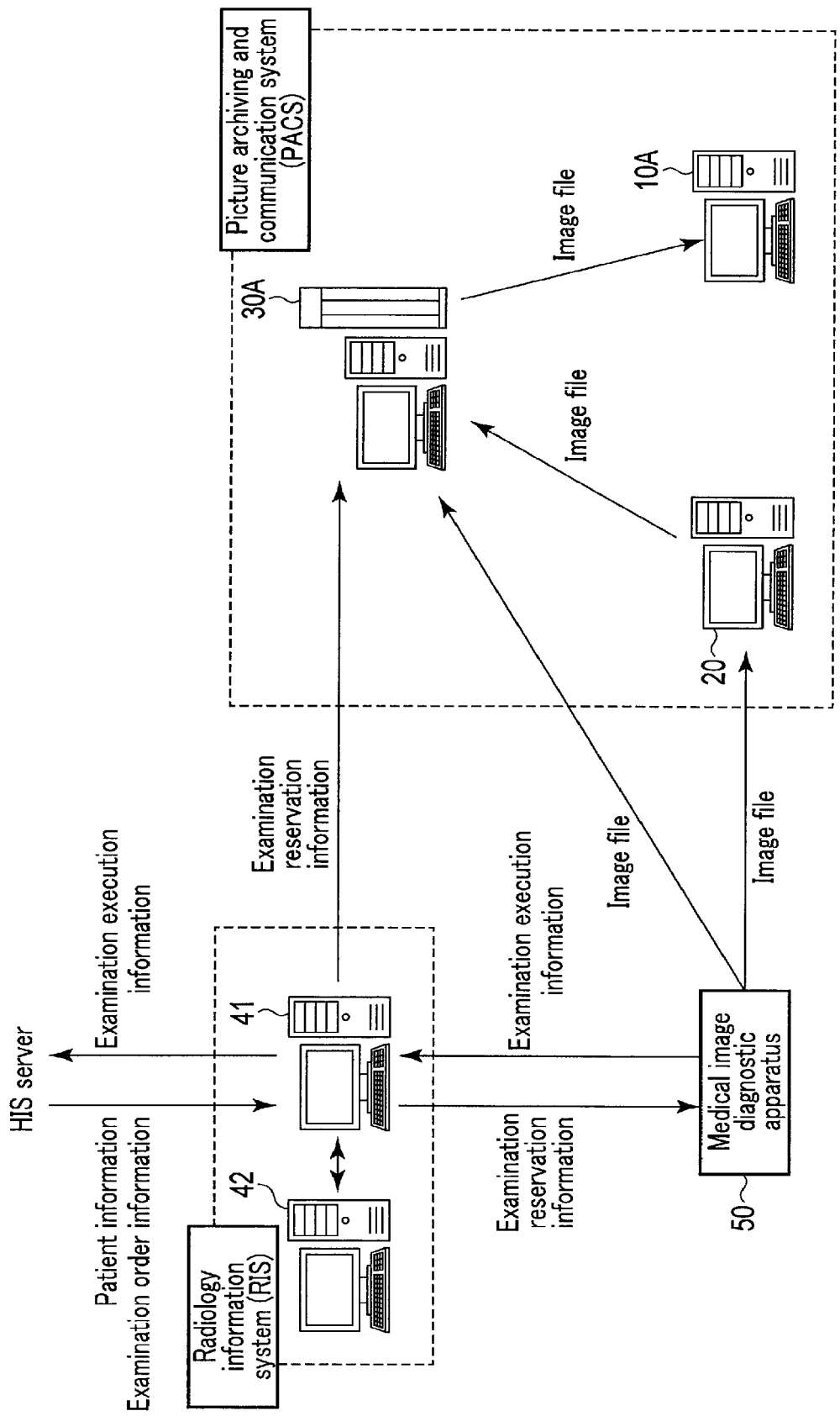
F I G. 12

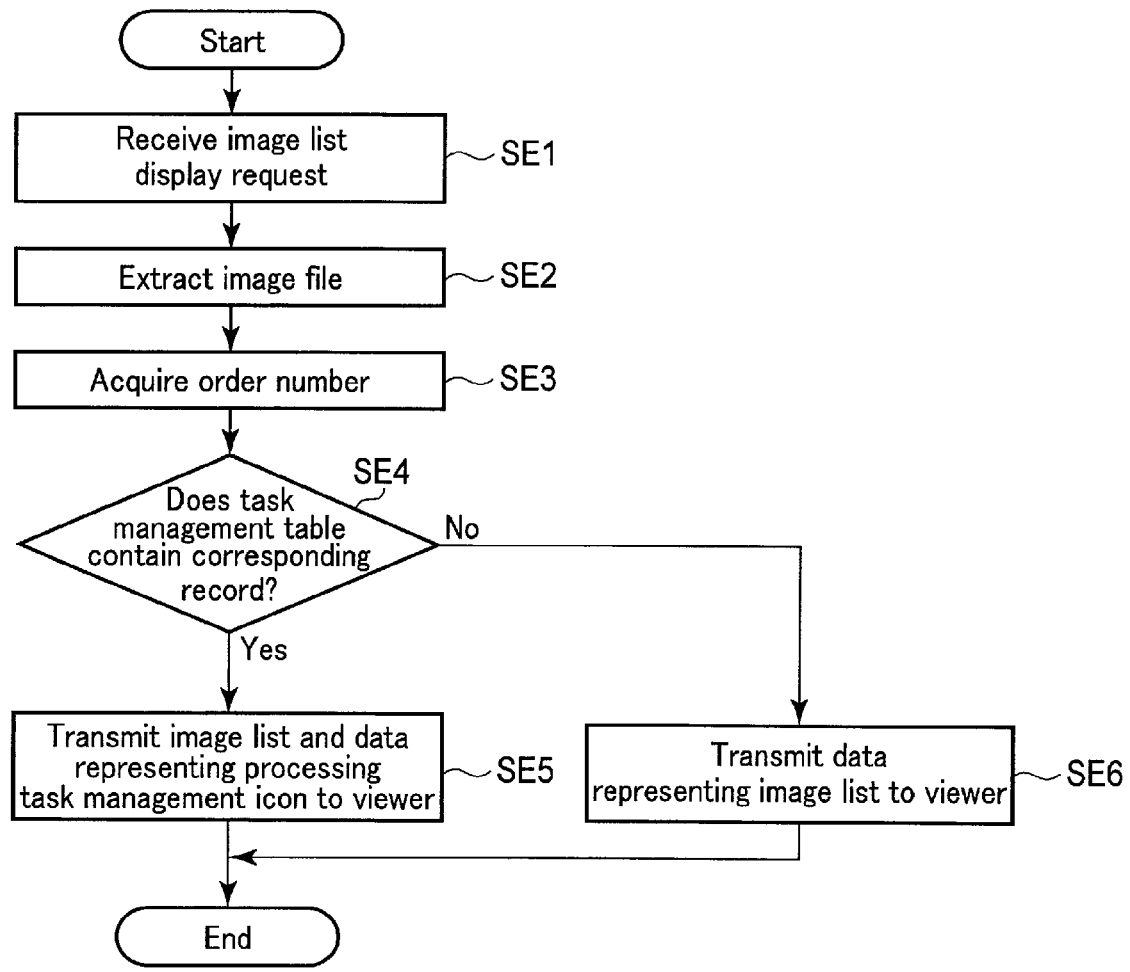
F I G. 16

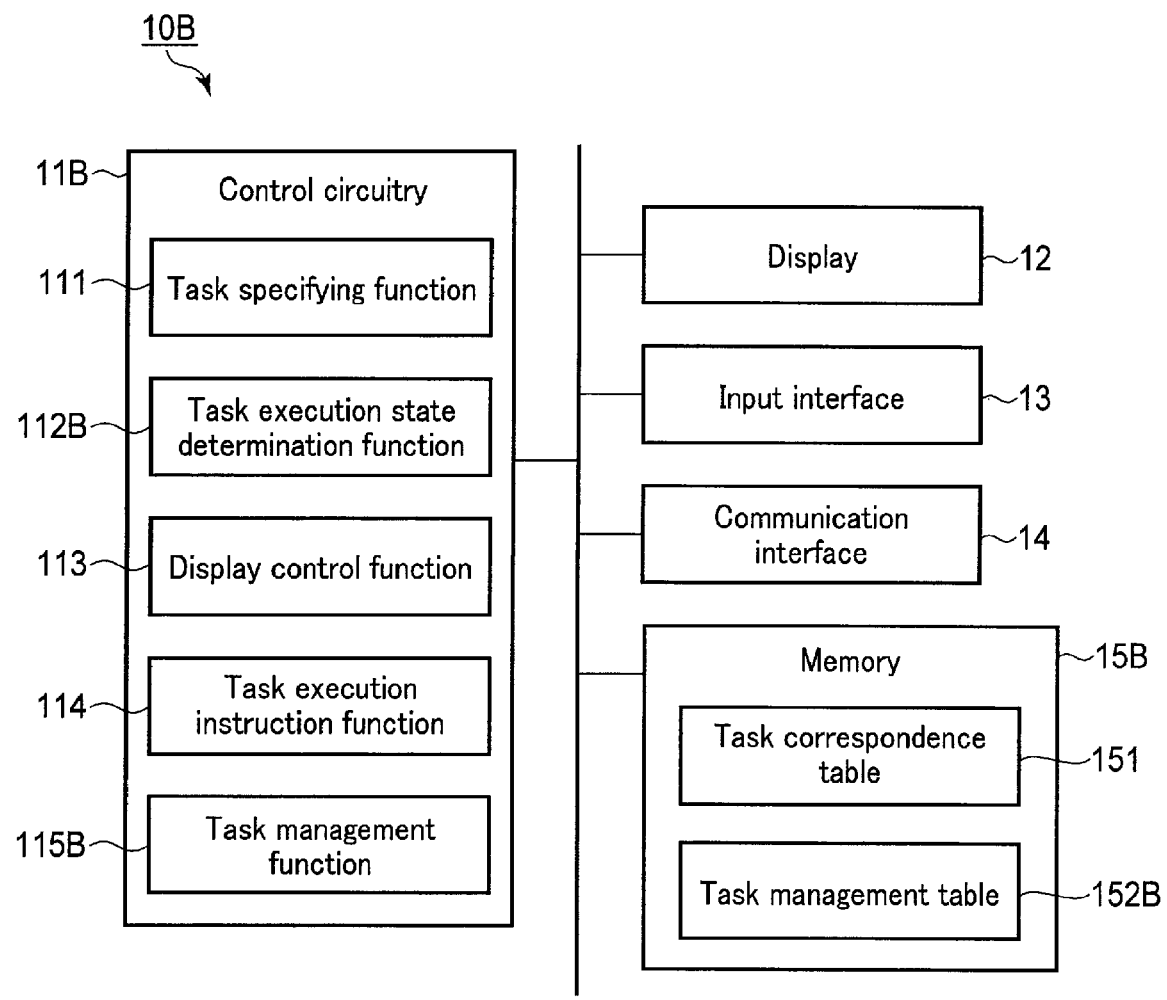
F I G. 20

| Examination UID | Processing task | State information |
|---|---|---|
| 0001 | Large intestine analysis | Unexecuted |
| 0001 | MPR | Unexecuted |
| ... | ... | ... |
| ... | ... | ... |
| ... | ... | ... |

F I G. 22

| Examination UID | Processing task | State information |
|---|---|---|
| 0001 | Large intestine analysis | Unexecuted |
| 0001 | MPR | Executed |
| ... | ... | ... |
| ... | ... | ... |
| ... | ... | ... |

F I G. 24

MEDICAL IMAGE DISPLAY APPARATUS

CROSS-REFERENCE TO RELATED APPLICATIONS

This application is based upon and claims the benefit of priority from the prior Japanese Patent Application No. 2017-015373, filed Jan. 31, 2017, the entire content is incorporated herein by reference.

FIELD

Embodiments described herein relate generally to a medical image display apparatus.

BACKGROUND

For example, a workstation applies various types of image processing to medical images obtained by an X-ray diagnostic apparatus, MRI, and the like. Image processing includes, for example, measuring the size and the like of a tumor depicted in a medical image, analyzing the medical image to obtain a predetermined examination result, and three-dimensionally visualizing the medical image. An interpretation doctor sometimes performs such image processing at the time of radiographic interpretation. Usually, however, an examination technician performs such image processing based on the contents of an examination request in consideration of the efficiency of radiographic interpretation before radiographic interpretation by an interpretation doctor. A PACS (Picture Archiving and Communication System) manages images obtained by applying predetermined image processing to medical images obtained by X-ray diagnostic apparatuses, MRIs, and the like in the same manner as for the medical images obtained by X-ray diagnostic apparatuses, MRIs, and the like.

For example, an examination technician sometimes forgets to execute image processing before radiographic interpretation. At the time of radiographic interpretation, an interpretation doctor sometimes performs radiographic interpretation by referring to processed images depending on the disease condition. However, information indicating the execution state of this image processing is not managed. This makes it difficult for the interpretation doctor to notice the omission of execution of image processing.

BRIEF DESCRIPTION OF THE DRAWING

FIG. 1 is a view showing a medical information system including a medical image display apparatus according to the first embodiment;

FIG. 5 is a view showing a task correspondence table according to the embodiment;

FIG. 6 is a view showing a task management table according to the embodiment;

FIG. 7 is a flowchart showing a procedure in which the control circuitry according to the first embodiment determines, in response to an image list display request, whether a processing task has been executed, and displays image data representing the determination result on a display;

FIG. 9 is a view showing a task management table according to the embodiment;

FIG. 12 is a view showing a medical information system including a medical image display apparatus according to the second embodiment;

FIG. 16 is a flowchart showing a procedure in which the control circuitry according to the second embodiment transmits image data representing whether a processing task has been executed to the viewer in response to an image list display request;

FIG. 20 is a block diagram showing an example of the arrangement of the medical image display apparatus according to the modification;

FIG. 22 is a view showing a task management table according to the modification;

FIG. 24 is a view showing a task management table according to the modification.

DETAILED DESCRIPTION

Figure 2:
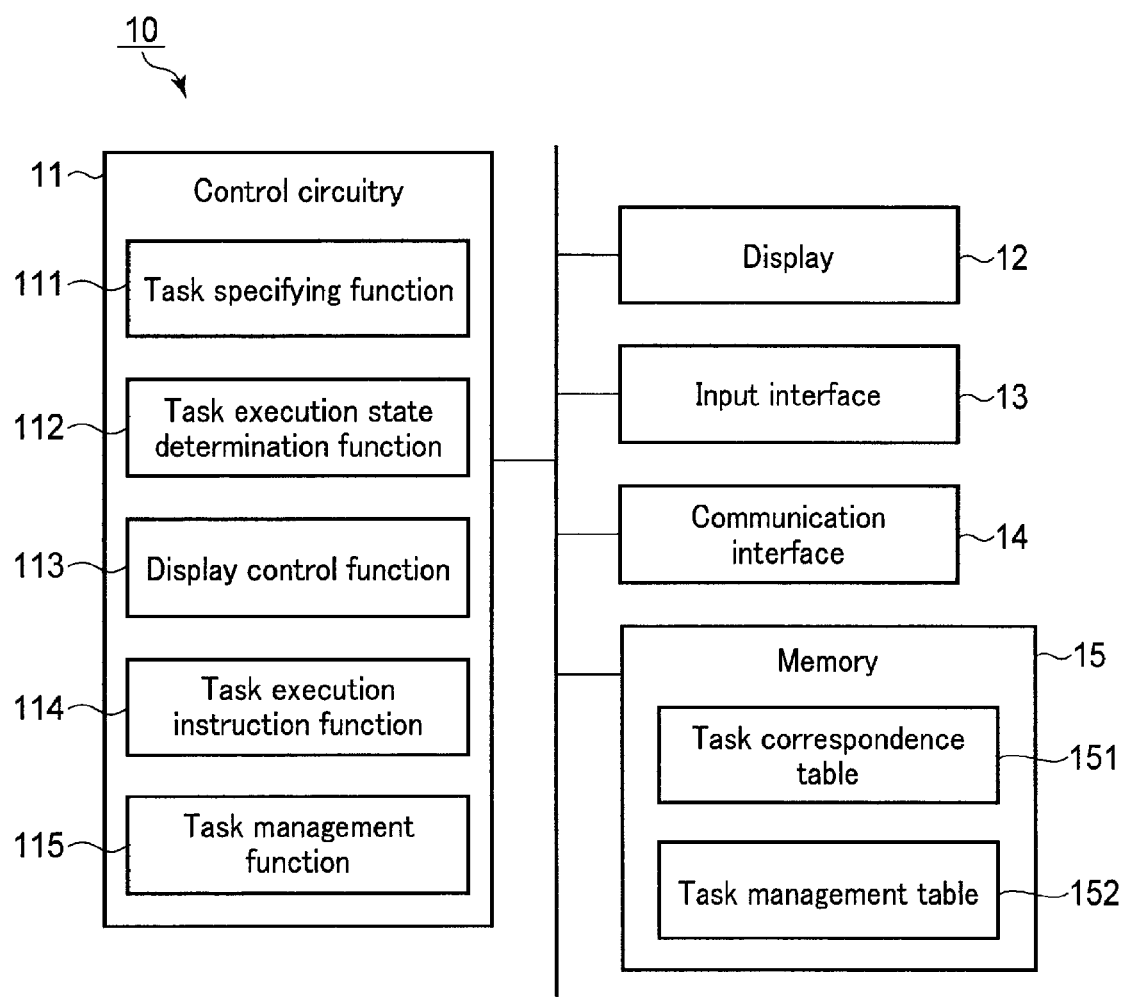
FIG. 2 is a block diagram showing the arrangement of a medical image display apparatus according to the first embodiment.

In general, according to one embodiment, a medical image display apparatus comprising a memory and processing circuitry. The memory configured to store a task management table associating a processing task executed for a medical image with state information representing whether or not the processing task has been executed. The processing circuitry configured to extract, from the task management table, state information that is associated with a processing task for a medical image requested to be displayed, and display, based on the extracted state information, information indicative of whether or not a processing task has been executed for the requested medical image.

First Embodiment

The first embodiment will be described below with reference to the accompanying drawings.

FIG. 1 is a schematic view showing a medical information system including a medical image display apparatus 10 according to the first embodiment. The medical information system shown in FIG. 1 includes the medical image display apparatus 10, a workstation 20, an image archiving server 30, an HIS (Hospital Information System) server, an RIS (Radiology Information System) server 41, an RIS terminal 42, and a medical image diagnostic apparatus 50. The medical image display apparatus 10, the workstation 20, the image archiving server 30, the HIS server, the RIS server 41, the RIS terminal 42, and the medical image diagnostic apparatus 50 are connected to a local network to transmit information to predetermined apparatuses and receive information transmitted from predetermined apparatuses. Note that the medical information system may be connected to an external network in addition to or in place of the local network.

Referring to FIG. 1, the medical image display apparatus 10, the workstation 20, and the image archiving server 30 are some of the elements constituting a PACS (Picture Archiving and Communication System). The RIS server 41 and the RIS terminal 42 are some of the elements constituting an RIS (Radiology Information System).

In the RIS, the RIS server 41 manages information concerning radiographic examination services. Information concerning radiographic examination services includes patient information, examination order information, and irradiation records. Patient information and examination order information are information output from the HIS server to the RIS server 41. Patient information contains patient IDs, patient names, sexes, body heights, body weights, ages, blood types, and the like. Examination order information contains order numbers that can identify examinations, patient IDs, examination scheduled dates and times, examination types, examination regions, request source information, and the like. An order number is a number issued when examination order information is input, and is, for example, an identifier for uniquely identifying examination order information within one hospital. A patient ID is assigned for each patient, and is, for example, an identifier for uniquely specifying a patient within one hospital. Examination types include X-ray examination, CT (Computed Tomography) examination, MR (Magnetic Resonance) examination, and RI (Radio Isotope) examination. Examination regions include ABDOMEN, BRAIN, and CHEST. Request source information contains clinical department names, attending doctor names, and the like. An irradiation record is, for example, various types of setting information set in the medical image diagnostic apparatus 50 in past examinations.

Upon receiving patient information and examination order information output from the HIS server, the RIS server 41 generates examination reservation information necessary to make the medical image diagnostic apparatus 50 operate based on the received patient information and examination order information.

At this time, the RIS server 41 generates examination reservation information based on an irradiation record in addition to the received patient information and examination order information. In addition, the RIS server 41 receives a radiographic examination request based on patient information and examination order information from the RIS terminal 42, and generates examination reservation information based on the received radiographic examination request. The RIS server 41 transmits the generated examination reservation information to the medical image diagnostic apparatus 50. Note that the examination reservation information contains information necessary to execute an examination, for example, an order number, patient ID, examination type, procedure, imaging region, body posture, and imaging direction.

The RIS server 41 receives examination execution information concerning an examination executed in accordance with examination reservation information from the medical image diagnostic apparatus 50. The RIS server 41 outputs the received examination execution information to the HIS server.

The medical image diagnostic apparatus 50 executes an examination based on the examination reservation information transmitted from the RIS server 41. The medical image diagnostic apparatus 50 includes, for example, an X-ray computed tomography apparatus, X-ray diagnostic apparatus, magnetic resonance imaging apparatus, nuclear medicine diagnostic apparatus, and ultrasonic diagnostic apparatus. The medical image diagnostic apparatus 50 generates medical images by executing an examination. Medical images include, for example, an X-ray CT image, X-ray image, MRI image, nuclear medicine image, and ultrasonic image. The medical image diagnostic apparatus 50 executes a processing task that defines predetermined image processing for a medical image in accordance with an instruction input from the RIS terminal 42 by, for example, an examination technician.

Image processing includes, for example, basic image processing such as MPR (Multiplanar Reconstruction) processing and VR (Volume Rendering) processing and applied image processing such as large intestine analysis, pulmonary nodule analysis, liver region/segmentation analysis, EP planning, and stent planning. When a processing task is executed, a secondary capture image, GSPS (Grayscale Softcopy Presentation State) information, and/or DICOM SR (Structured Report) are generated as a result of executing the processing task. GSPS information is, for example, note information to be superimposed on an image. DICOM SR is, for example, information representing analysis information such as various types of measured values obtained by executing a processing task. Although a processing task uses an application mainly generated by a predetermined application vender, the task may use a simpler measurement tool, a tool for observing a specific region using a specific method, or the like.

The medical image diagnostic apparatus 50 generates a medical image file by converting a generated medical image into a format complying with the DICOM (Digital Imaging and Communication in Medicine) standard. In addition, the medical image diagnostic apparatus 50 converts information generated by executing a processing task into a file in a format complying with, for example, the DICOM standard. This embodiment will exemplify a case in which for example, a secondary capture image is generated by executing a processing task. A capture image is converted into an SC (Secondary Capture) image file complying with the DICOM standard.

A medical image file contains image data concerning a medical image and additional information that classifies the image data and indicates the origin and the like of the image data. Additional information in a medical image file includes, for example, information for specifying a medical image, such as an order number, examination UID, series UID, patient ID, modality code, series NO., and series description corresponding to the generated medical image. An examination UID is an identifier capable of uniquely specifying an examination. A series UID is an identifier that is acquired for, for example, each imaging region or imaging condition, and is capable of uniquely specifying a series of images. A modality code is an identifier for specifying an image type. For example, "CT", "MR", and "US" are defined as such identifiers. Note that "CT", "MR", and "US" respectively indicate medical images obtained by an X-ray computed tomography apparatus, magnetic resonance imaging apparatus, and ultrasonic diagnostic apparatus. A series NO. is an identifier capable of uniquely specifying a series of images that are acquired for, for example, each imaging region or imaging condition. A series NO. is defined for, for example, each medical facility. A series description represents the contents of a special instruction, if any, which an examination technician should inform to a doctor at the time of an examination (imaging).

An SC image file contains image data concerning a capture image and additional information that classifies the image data and indicates the origin and the like of the medical image data. Additional information in an SC image file includes, for example, information for specifying a medical image, such as an order number, examination UID, series UID, patient ID, modality code, series NO., series description, which correspond to the generated capture image, and information capable of specifying an executed processing task. Note that "SC" representing that the corresponding image is an SC image is set in the modality code contained in additional information in an SC image file. Information capable of specifying a processing task includes, for example, a processing task name. The medical image diagnostic apparatus 50 outputs the generated medical image file and SC image file to the workstation 20 and the image archiving server 30.

The image archiving server 30 archives medical image files and SC image files output from the medical image diagnostic apparatus 50 in a predetermined storage device of the image archiving server 30, and outputs archived medical image files and SC image files in accordance with requests.

The medical image display apparatus 10 displays a medical image and a capture image respectively based on a medical image file and an SC image file archived in the image archiving server 30.

The workstation 20 executes a predetermined processing task for a medical image contained in a medical image file to generate a capture image. The workstation 20 generates an SC image file by converting the generated capture image into a format complying with, for example, the DICOM standard.

The medical image display apparatus 10 and the workstation 20 will be described in detail below.

The medical image display apparatus 10 according to the first embodiment assumes, for example, the role of a DICOM viewer. FIG. 2 is a block diagram showing an example of the arrangement of the medical image display apparatus 10 according to the first embodiment. The medical image display apparatus 10 shown in FIG. 2 includes control circuitry 11, a display 12, an input interface 13, a communication interface 14, and a memory 15. The control circuitry 11, the display 12, the input interface 13, the communication interface 14, and the memory 15 are communicably connected to each other via, for example, a bus.

The control circuitry 11 is a processor functioning as the main unit of the medical image display apparatus 10. The control circuitry 11 executes various operation programs stored in the memory 15 or the like to implement functions corresponding to the programs.

The display 12 includes, for example, a display device such as a CRT display, liquid crystal display, organic EL display, LED display, plasma display, or another arbitrary display known in this technical field. The display 12 displays various types of information via a display device.

The input interface 13 is implemented by, for example, a mouse, a keyboard, and a touch pad having an operation screen that the operator touches to input an instruction. The input interface 13 receives various types of instructions from the operator. The input interface 13 is connected to the control circuitry 11 via, for example, a bus. The input interface 13 converts an operation instruction input from the operator into an electrical signal and outputs it to the control circuitry 11. Note that in this specification, the input interface 13 is not limited to the one including a physical operation component such as a mouse or keyboard. For example, the input interface 13 includes electrical signal control circuitry that receives an electrical signal corresponding to an operation instruction input from an external input device provided independently of the medical image display apparatus and outputs the electrical signal to the control circuitry 11.

The communication interface 14 communicates data with external apparatuses such as the workstation 20, the image archiving server 30, and the RIS server 41 of the radiology information system, to which the communication interface 14 is connected via the network shown in FIG. 1 or the like. Although communication with the external device may be based on any standard, for example, the DICOM standard may be used.

The memory 15 is a storage device such as an HDD (Hard Disk Drive), SSD (Solid State Drive), or integrated circuitry storage device that stores various types of information. In addition, the memory 15 may be, for example, a CD-ROM drive, a DVD drive, or a drive device that reads and writes various types of information to and from a portable storage medium such as a flash memory. The memory 15 stores a task correspondence table 151 and a task management table 152.

The task correspondence table 151 is a master table that associates predetermined "clinical keywords" expected to be contained in examination reservation information output from the RIS server 41 with "processing tasks" to be executed in correspondence with examinations specified by the examination reservation information. A clinical keyword is, for example, a character string capable of evoking an associated "processing task" and is constituted by one or more words. When a "processing task" is "large intestine analysis", a clinical keyword is represented as, for example, "CT, large intestine, cancer". Each information in the task correspondence table 151 may be registered in advance or may be manually registered via the input interface 13.

The task management table 152 is a table that associates each "processing task" to be executed for a requested examination with "state information" representing whether the "processing task" has been executed, and is a table for managing whether each processing task has been executed. Each information in the task management table 152 is registered, for example, at a predetermined timing after a "processing task" necessary to achieve the purpose of a requested examination is specified. In addition, each information in the task management table 152 is updated, for example, at a predetermined timing after a "processing task" registered in the task management table 152 is executed. Note that an examination technician, an interpretation doctor, and the like may, for example, additionally register a missing processing task for predetermined examination preservation information or may delete an excess processing task in or from the task management table 152 via the input interface 13.

The control circuitry 11 according to the first embodiment implements various types of functions shown in FIG. 2 by executing operation programs read out from the memory 15. That is, the control circuitry 11 includes a task specifying function 111, a task execution state determination function 112, a display control function 113, a task execution instruction function 114, and a task management function 115. The first embodiment will exemplify a case in which the task specifying function 111, the task execution state determination function 112, the display control function 113, the task execution instruction function 114, and the task management function 115 are implemented by a single processor. However, this is not exhaustive. For example, control circuitry may be formed by combining a plurality of independent processors, and the task specifying function 111, the task execution state determination function 112, the display control function 113, the task execution instruction function 114, and the task management function 115 may be implemented by causing the respective processors to execute operation programs.

The task specifying function 111 is a function for specifying a processing task to be executed based on examination reservation information transmitted from the RIS server 41. When the task specifying function 111 is executed, the control circuitry 11 collates the character string contained in examination reservation information transmitted from the RIS server 41 with clinical keywords registered in the task correspondence table 151. If a clinical keyword registered in the task correspondence table 151 is contained in the examination reservation information, the control circuitry 11 determines that a processing task is required for the examination reservation information transmitted from the RIS server 41. The control circuitry 11 extracts a processing task associated with the clinical keyword from the processing tasks registered in the task correspondence table 151. This will specify a processing task to be executed from the examination reservation information transmitted from the RIS server 41.

The task execution state determination function 112 is a function for determining whether the processing task specified by the execution of the task specifying function 111 has been executed. When the task execution state determination function 112 is executed, the control circuitry 11 determines, based on additional information in a medical image file and additional information in an SC image file, whether a processing task registered in the task management table 152 has been executed.

The display control function 113 is a function for controlling the display 12 to display whether a processing task has been executed. When the display control function 113 is executed, the control circuitry 11 generates image data representing whether the processing task has been executed, in accordance with a determination result obtained by the task execution state determination function 112. The control circuitry 11 displays an image based on generated image data on the display 12.

The task execution instruction function 114 is a function for instructing an external apparatus such as the workstation 20 via the communication interface 14 to execute a processing task registered in the task management table 152.

The task management function 115 is a function for managing records in the task management table 152. When the task management function 115 is executed, the control circuitry 11 registers the processing task specified by the task specifying function 111 in the task management table 152. The control circuitry 11 also updates the state information of a processing task registered in the task management table 152 by using the determination result obtained by the task execution state determination function 112. In addition, when a predetermined processing task that has not been executed is executed, the control circuitry 11 updates the state information of the corresponding processing task in the task management table 152 to "executed" indicating that the processing task has been executed.

Upon receiving an image list display request, the control circuitry 11 also monitors whether a processing task requested by, for example, an examination technician to be executed in the examination has been executed, while displaying the image list requested to be displayed. If, for example, an SC image file necessary for the requested examination is output to the image archiving server 30, the control circuitry 11 determines that the processing task necessary for the requested examination has been executed. The control circuitry 11 then updates the state information of the corresponding processing task to "executed" in the task management table 152.

Figure 3:
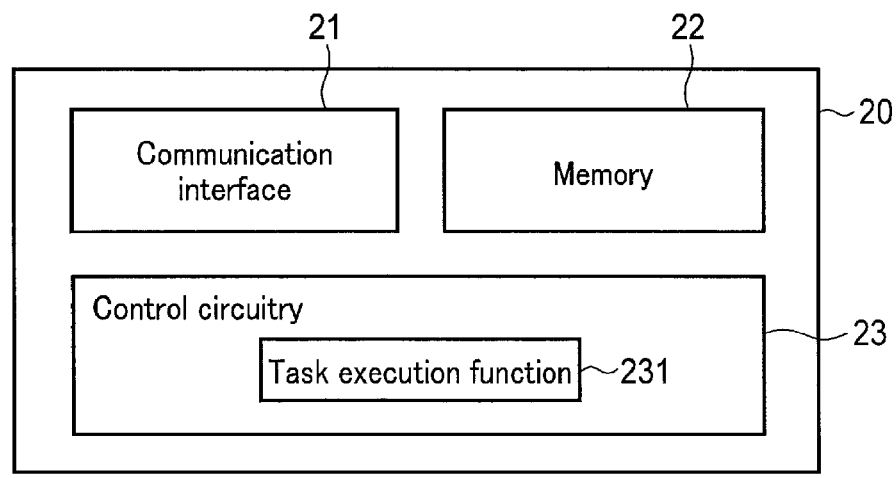
FIG. 3 is a block diagram showing the arrangement of a workstation according to the first embodiment.

The workstation 20 according to the first embodiment executes a processing task suitable for the purpose of interpretation with respect to a predetermined medical image in accordance with an instruction from the medical image display apparatus 10. FIG. 3 is a block diagram showing the arrangement of the workstation according to this embodiment. The workstation 20 shown in FIG. 3 includes a communication interface 21, a memory 22, and control circuitry 23.

The communication interface 21 communicates data with external apparatuses such as the medical image display apparatus 10, the image archiving server 30, and the medical image diagnostic apparatus 50 connected to the communication interface 21 via the network shown in FIG. 1 or the like.

The memory 22 is a storage device such as an HDD, SSD, or integrated circuitry storage device that stores various types of information. In addition, the memory 22 may be, for example, a CD-ROM drive, a DVD drive, or a drive device that reads and writes various types of information to and from a portable storage medium such as a flash memory. The memory 22 stores medical image files and SC image files.

The control circuitry 23 is a processor functioning as the main unit of the workstation 20. The control circuitry 23 also implements a task execution function 231 shown in FIG. 3 by executing an operation program read out from the memory 22.

The task execution function 231 is a function for executing a processing task in accordance with an instruction from the medical image display apparatus 10. When the task execution function 231 is executed, the control circuitry 23 reads out an image processing program concerning a processing task corresponding to the instruction from the memory 22. The control circuitry 23 executes the processing task corresponding to the instruction from the medical image display apparatus 10 by executing the read image processing program, thereby generating a capture image. The control circuitry 23 generates an SC image file by converting the generated capture image into a format complying with the DICOM standard.

Figure 4:
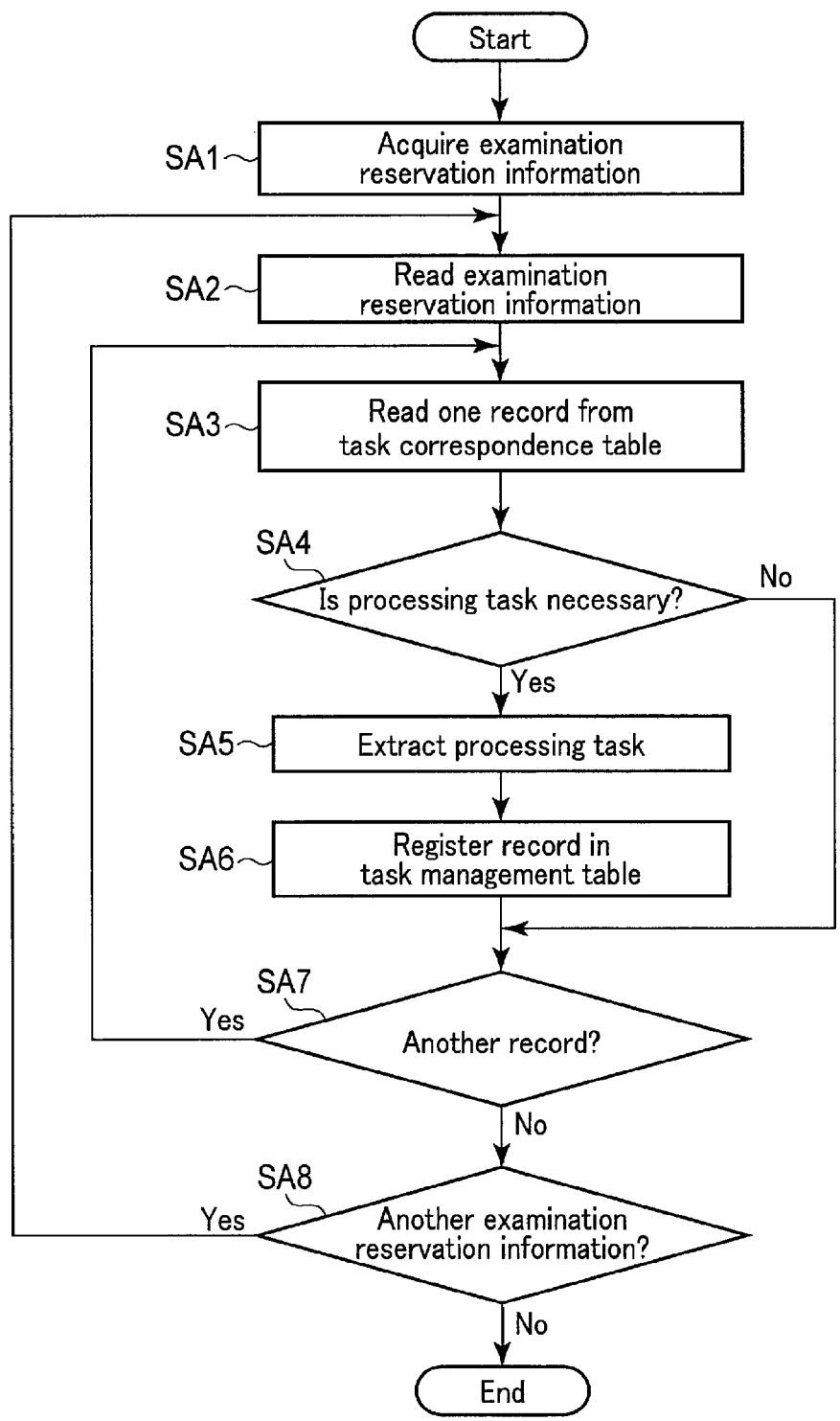
FIG. 4 is a flowchart showing a procedure in which control circuitry according to the first embodiment specifies a processing task.

An operation in which the medical image display apparatus 10 having the above arrangement specifies a processing task will be described in accordance with the processing procedure in the control circuitry 11 shown in FIG. 4. FIG. 4 is a flowchart showing an example of a procedure in which the control circuitry 11 according to the first embodiment specifies a processing task. For the sake of clarity, assume that processing tasks necessary for a requested examination are "MPR" and "large intestine analysis". Assume also that an examination technician has executed "MPR" at the time of imaging examination, but has not been executed "large intestine analysis". In addition, assume that the series description contained in each of pieces of additional information in a medical image file and an SC image file contains a processing task name as the name of a processing task. Furthermore, assume that the processing task name is used as information capable of specifying a processing task.

The control circuitry 11 executes the task specifying function 111 upon receiving, via the input interface 13, an activation instruction to activate a predetermined application for displaying a medical image and a capture image. The control circuitry 11 executes the task specifying function 111 to acquire examination reservation information from the RIS server 41 (step SA1). The examination reservation information to be acquired is the one generated in a predetermined period, for example, the period between the day when an interpretation doctor performs radiographic interpretation and the day one week before the day of radiographic interpretation.

The control circuitry 11 reads one of the acquired pieces of examination reservation information (step SA2). Assume that in this case, the read examination reservation information contains order number "000001", patient ID "00001", apparatus "X-ray CT examination", procedure "CT colonography", imaging region "large intestine", body posture "none specified", and imaging direction "none specified".

Upon reading examination reservation information in step SA2, the control circuitry 11 reads one record from the task correspondence table 151 shown in FIG. 5 (step SA3).

In the task correspondence table 151 shown in FIG. 5, for example, processing task "large intestine analysis" corresponds to clinical keyword "CT, large intestine, colonography". Processing task "pulmonary nodule analysis" corresponds to clinical keyword "CT, lung, nodule". Processing task "liver region/segmentation analysis" corresponds to clinical keyword "CT, liver, tumor". Processing task "EP planning" corresponds to clinical keyword "CT, atrium, pulmonary artery, arrhythmia". Processing task "stent planning" corresponds to clinical keyword "CT, aortic aneurysm, stent". Processing task "MPR" corresponds to clinical keyword "CT". Processing task "MPR" corresponds to clinical keyword "MRI".

The control circuitry 11 reads the first row record, i.e., the record of clinical keyword "CT, large intestine, colonography" and processing task "large intestine analysis", shown in, for example, FIG. 5.

The control circuitry 11 determines whether processing task "large intestine analysis" set in the record read in step SA3 is necessary for the examination reservation information read in step SA2 (step SA4). More specifically, the control circuitry 11 collates apparatus "X-ray CT examination", procedure "CT colonography", imaging region "large intestine", body posture "none specified", and imaging direction "none specified", i.e., the character string contained in the examination reservation information, with clinical keyword "CT, large intestine, colonography" contained in the read record.

Because clinical keyword "CT, large intestine, colonography" is contained in the character string contained in the examination reservation information, the control circuitry 11 determines that the processing task is necessary for the examination reservation information (YES in step SA4). The control circuitry 11 then extracts processing task "large intestine analysis" associated with the clinical keyword from the task correspondence table 151 (step SA5).

Upon extracting processing task "large intestine analysis" from the task correspondence table 151 in step SA5, the control circuitry 11 executes the task management function 115. The control circuitry 11 executes the task management function 115 to register a record concerning extracted processing task "large intestine analysis" in the task management table 152, as shown in FIG. 6 (step SA6).

That is, the control circuitry 11 registers the record containing order number "000001", processing task "large intestine analysis", and state information "unexecuted" in the task management table 152.

The control circuitry 11 determines whether the records registered in the task correspondence table 151 include another record for which the necessity to execute the processing task has not been determined (step SA7).

If there is another record for which the necessity to execute a processing task has not been determined (YES in step SA7), the control circuitry 11 reads one record for which the necessity to execute a processing task has not been determined from the task correspondence table 151 (step SA3), and executes the processing from step SA4 again.

For example, because the necessity to execute processing task "MPR" shown in FIG. 5 has not been determined, the control circuitry 11 reads out a record containing processing task "MPR" (step SA3). The control circuitry 11 collates clinical keyword "CT" with the character string contained in examination reservation information (step SA4). Because the examination reservation information contains clinical keyword "CT", the control circuitry 11 extracts processing task "MPR" from the task correspondence table 151 (step SA5). As shown in FIG. 6, the control circuitry 11 registers a record concerning extracted processing task "MPR" in the task management table 152 (step SA6). That is, the control circuitry 11 registers a record containing order ID "000001", processing task "MPR", and state information "unexecuted" in the task management table 152.

If there is not another record for which the necessity to execute a processing task has not been determined (NO in step SA7), the control circuitry 11 determines whether there is another examination reservation information for which the necessity to execute a processing task has not been determined (step SA8).

If there is another examination reservation information for which the necessity to execute a processing task has not been determined (YES in step SA8), the control circuitry 11 reads one piece of examination reservation information (step SA2), and executes the processing from step SA3 to step SA7 again.

If there is not another examination reservation information for which the necessity to execute a processing task has not been determined (NO in step SA8), the control circuitry 11 finishes the processing by the task specifying function 111.

The next will describe an operation in which the medical image display apparatus 10 displays state information registered in the task management table 152 on the display 12 in response to an image list display request. FIG. 7 is a flowchart showing a procedure in which the control circuitry 11 according to the first embodiment determines, in accordance with an image list display request, whether a processing task has been executed, and displays image data representing the determination result on the display 12. Assume that in the following description, an image list display request is implemented by designating, for example, a patient ID and an examination UID.

The control circuitry 11 receives an image list display request via the input interface 13 (step SB1). More specifically, first of all, an interpretation doctor or the like designates a patient as an examination target requested via the input interface 13. At this time, for example, the control circuitry 11 reads out a medical image file and an SC image file from the image archiving server 30 by using the patient ID of the designated patient as a key. Additional information in the read medical image file and additional information in the read SC image file each include an order number, an examination UID, and a series UID in addition to the patient ID.

Figure 8:
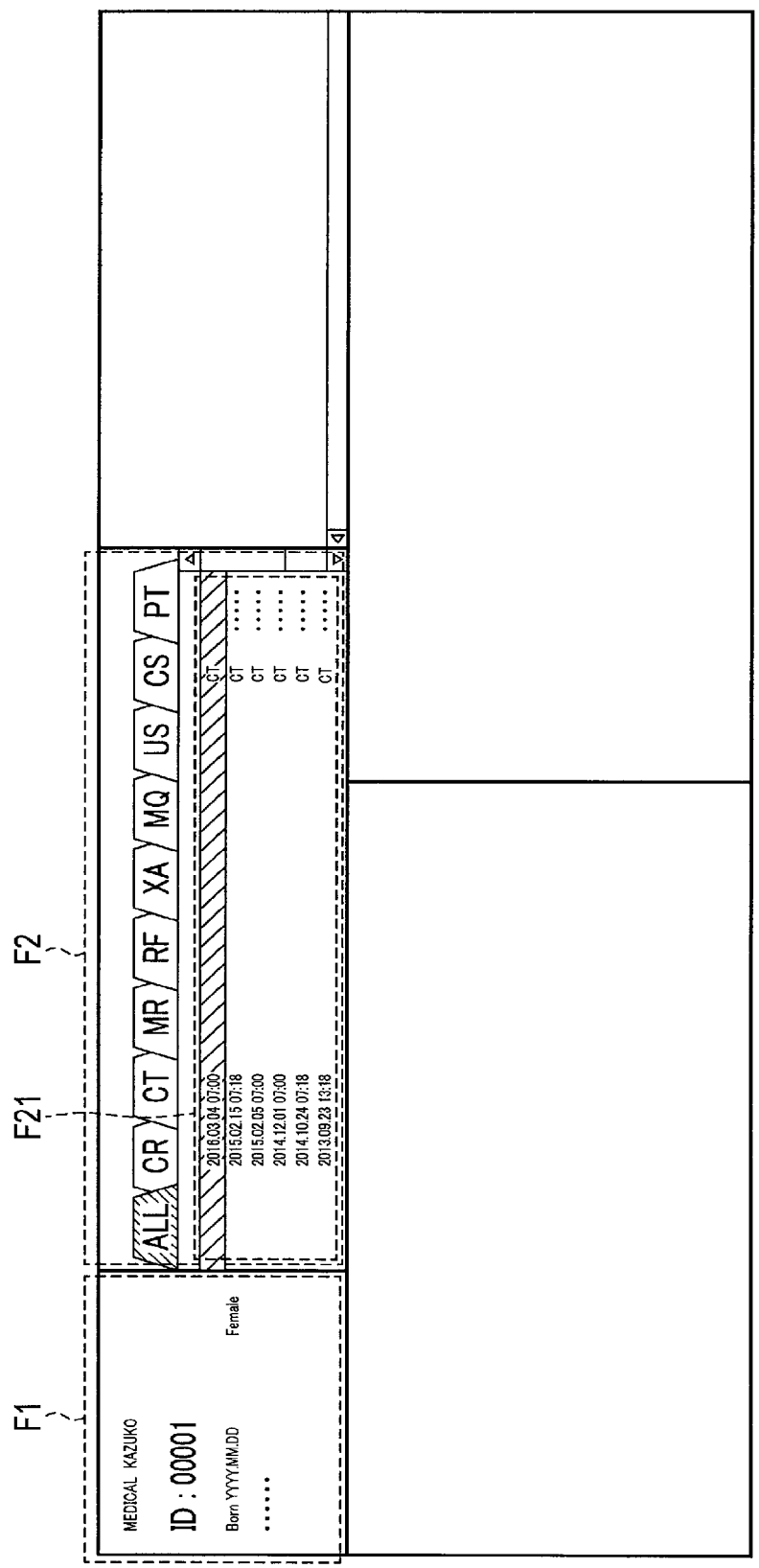
FIG. 8 is a view showing a display screen displaying patient information and an examination list that are read out based on a patient ID as a key on the display according to the first embodiment.

FIG. 8 is a view showing an example of a display screen, on the display 12 according to the first embodiment, which displays patient information and an examination list read out based on the patient ID as a key. As shown in FIG. 8, the display screen includes a patient information display area F1 displaying the patient information of the patient identified by a patient ID and an examination information display area F2 displaying a list of examinations executed for the patient displayed in the patient information display area F1. The examination information display area F2 displays an examination selection area F21 for selection of a predetermined examination for each examination date and time when the examination has been executed. FIG. 8 shows the patient information and the examination list read out based on patient ID "00001" as a key.

As shown in FIG. 8, the control circuitry 11 executes the task execution state determination function 112 for the patient indicated by patient ID "00001" upon reception of an image list display request concerning the examination executed "at 7 a.m. on Mar. 4, 2016". The control circuitry 11 executes the task execution state determination function 112 to extract a medical image file and an SC image file containing the examination UID assigned to this examination, for example, "0001", from the medical image files and the SC image files read out in advance from the image archiving server 30 based on patient ID "00001" (step SB2).

Note that the control circuitry 11 may read out only additional information in the medical image file and the SC image file from the image archiving server 30 based on the patient ID of the designated patient as a key. At this time, the control circuitry 11 reads out only those of image data concerning the medical image and image data concerning the SC image which concern the designated examination UID at the time of designation of the patient ID and the examination UID from the image archiving server 30.

The control circuitry 11 acquires order number "000001" contained in additional information in the extracted medical image file or SC image file (step SB3).

The control circuitry 11 determines whether the record corresponding to acquired order number "000001" exists in task management table 152 (step SB4).

If the record corresponding to order number "000001" does not exist in the task management table 152 (NO in step SB4), the control circuitry 11 displays an image list concerning the medical image file extracted in step SB2 in an image list display area F3 shown in FIG. 8 (step SB11).

If the record corresponding to order number "000001" exists in the task management table 152 (YES in step SB4), the control circuitry 11 reads one record corresponding to order number "000001" from the task management table 152 (step SB5).

The control circuitry 11 refers to additional information in the SC image file extracted in step SB2 so as to acquire the execution result of the processing task contained in the record read from the task management table 152 shown in FIG. 6 (step SB6). The control circuitry 11 acquires the execution result of processing task "large intestine analysis" contained in the record corresponding to order number "000001" shown in, for example, FIG. 6. More specifically, the control circuitry 11 acquires the number of SC image files, of the SC image files corresponding to order number "000001", in each of which information capable of specifying the processing task contained in the corresponding additional information represents processing task "large intestine analysis".

The control circuitry 11 determines whether the corresponding processing task has been executed by comparing the number of SC image files acquired in step SA6 with a number set in advance for each processing task (step SB7). More specifically, the control circuitry 11 determines whether processing task "large intestine analysis" has been executed by comparing the number of SC image files, of the SC image files corresponding to order number "000001", in each of which information capable of specifying the processing task contained in the corresponding additional information represents processing task "large intestine analysis" with a number set in advance for processing task "large intestine analysis".

If the SC image files corresponding to order number "000001" do not include any SC image file in which information capable of specifying the processing task contained in the corresponding additional information represents processing task "large intestine analysis", the control circuitry 11 determines that processing task "large intestine analysis" has not been executed (NO in step SB7). The control circuitry 11 then determines whether the records corresponding to order number "000001" in the task management table 152 include another record for which whether the processing task has been executed has not been determined (step SB9).

If the records corresponding to order number "000001" in the task management table 152 include another record for which whether the processing task has been executed has not been determined (YES in step SB9), the control circuitry 11 reads one record from the task management table 152 (step SB5), and executes the processing in and after step SB6 again.

The control circuitry 11 executes the processing in and after step SB6 again because the records corresponding to order number "000001" in the task management table 152 include another record for which whether the processing task has been executed has not been determined, i.e., a record corresponding to order number "000001" and processing task "MPR", as shown in FIG. 6.

More specifically, the control circuitry 11 acquires the number of SC image files, of the SC image files corresponding to order number "000001", in each of which information capable of specifying the processing task contained in the corresponding additional information represents processing task "MPR" (step SB6).

The control circuitry 11 determines whether processing task "MPR" has been executed by comparing the number of SC image files, of the SC image files corresponding to order number "000001", in each of which information capable of specifying the processing task contained in the corresponding additional information represents processing task "MPR" with a number set in advance for processing task "MPR" (step SB7).

If the number of SC image files, of the SC image files corresponding to order number "000001", in each of which information capable of specifying the processing task contained in the corresponding additional information represents processing task "MPR" is equal to a number set in advance for processing task "MPR", the control circuitry 11 determines that processing task "large intestine analysis" has been executed (YES in step SB7). The control circuitry 11 then updates the value of the state information of the record corresponding to order number "000001" and processing task "MPR" from "unexecuted" shown in FIG. 6 to "executed" shown in FIG. 9 in the task management table 152.

Note that the control circuitry 11 may determine in step SB7 whether a processing task has been executed based on GSPS information generated as a result of executing a processing task and/or the number of DICOM SRs or the like. In addition, the control circuitry 11 may update the state information of a processing task in the task management table 152 based on the number of SC image files for each processing task, GSPS information generated as a result of executing the processing task, and/or the number of DICOM SRs or the like.

If the records corresponding to order number "000001" in the task management table 152 do not include another record for which whether the processing task has been executed has not been determined (NO in step SB9), the control circuitry 11 executes display control function 113. The control circuitry 11 executes the display control function 113 to refer to the task management table 152 shown in FIG. 9 so as to generate, for, for example, each series, image data representing whether a processing task corresponding to order number "000001" linked to examination UID "0001" assigned to the examination designated by an image list display request has been executed, in accordance with the value of the state information of the processing task. The control circuitry 11 controls the display 12 to display the generated image data as an image processing state display icon in the image list display area F3 shown in FIG. 8 together with an image list concerning the medical image file (step SB10). An image processing state display icon is an icon capable of identifying whether a processing task concerning a predetermined order number has been executed.

Figure 10:
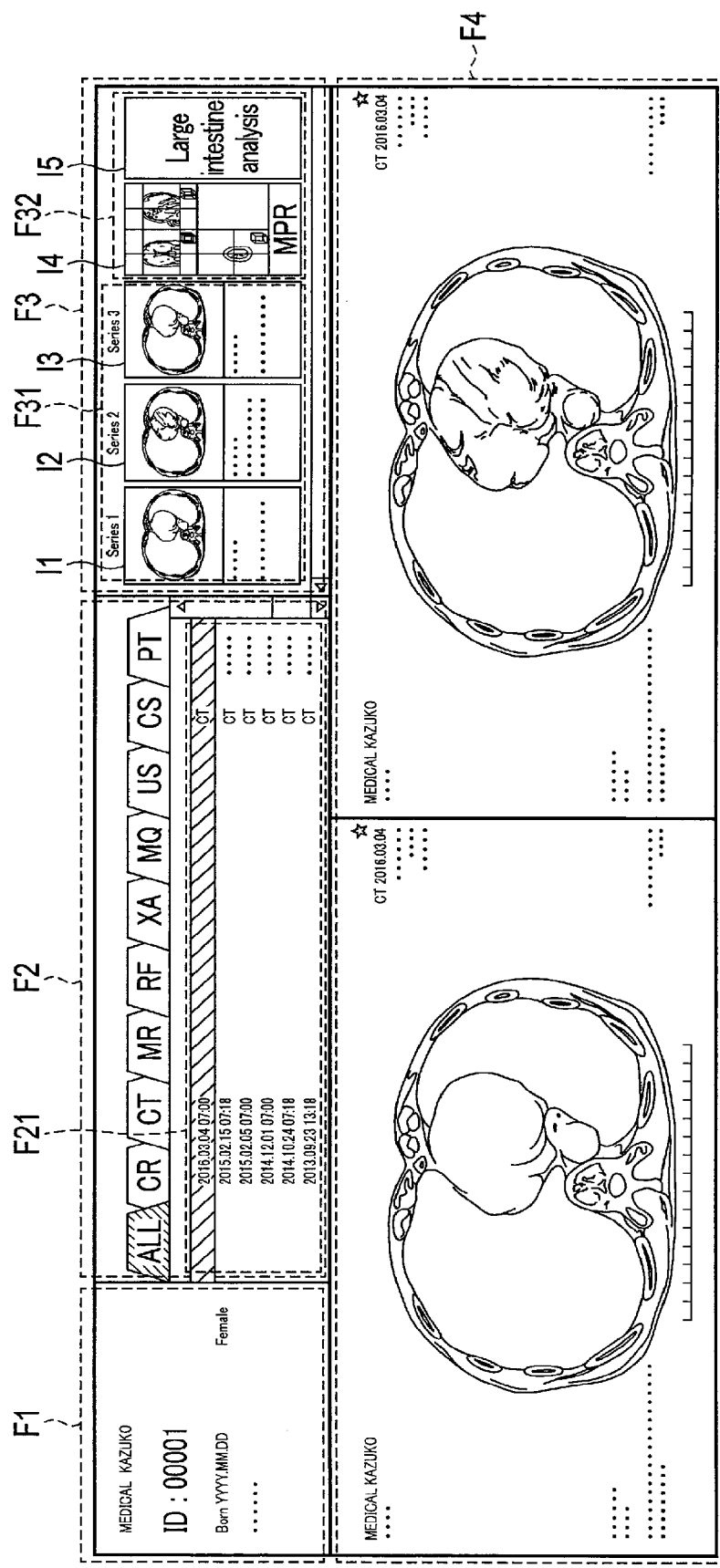
FIG. 10 is a view showing a display screen that is displayed on the display according to the first embodiment and includes icons each indicating whether the corresponding processing task has been executed.

FIG. 10 is a view showing an example of a display screen containing an image processing state display icon, which is displayed on the display 12 according to the first embodiment. The display screen shown in FIG. 10 includes, in addition to the patient information display area F1 and the examination information display area F2 shown in FIG. 8, the image list display area F3 displaying an image list and an image display area F4 sequentially displaying a plurality of medical images that can be radiographic interpretation candidates. The image list display area F3 shown in FIG. 10 includes a medical image display area F31 and an image processing state display area F32.

The medical image display area F31 is an area displaying a medical image display command icon associated with an image list for, for example, each series. A medical image display command icon is an icon displaying, for example, the first medical image of a predetermined series in a thumbnail form.

Referring to FIG. 10, the medical image display area F31 displays, for example, a medical image display command icon I1 associated with a plurality of medical image files belonging to series 1, medical image display command icon I2 associated with a plurality of medical image files belonging to series 2, and medical image display command icon I3 associated with a plurality of medical image files belonging to series 3. When a medical image display command icon is designated, for example, images represented by image data contained in a plurality of medical image files belonging to a predetermined series associated with the medical image display command icon are sequentially displayed in the image display area F4 a predetermined number of images at a time.

The image processing state display area F32 is, for example, an area displaying an image processing state display icon generated in accordance with the value of the state information of a processing task registered in the task management table 152. FIG. 10 shows an image processing state display icon generated in accordance with the value of the state information of a record extracted based on order number "000001" linked to examination UID "0001" assigned to the examination designated by an image list display request.

As shown in FIG. 10, for a processing task corresponding to state information "executed", the control circuitry 11 causes the display 12 to display, for example, an image processing state display icon I4 with which a capture image as a result of executing processing task "MPR" is associated. As shown in FIG. 10, the image processing state display icon I4 displays, for example, a representative capture image, of capture images generated as a result of executing processing task "MPR" in a thumbnail form. In addition, as shown in FIG. 10, the image processing state display icon I4 displays "MPR" to allow recognition of a generated capture image as a capture image generated as a result of executing processing task "MPR".

When the image processing state display icon I4 is designated, for example, the control circuitry 11 deploys an SC image display command icon for each series. An SC image display command icon is an icon displaying the first capture image of a predetermined series in a thumbnail form.

More specifically, when an SC image display command icon concerning series 1 is designated, the control circuitry 11 deploys a plurality of capture images generated as a result of executing processing task "MPR" with respect to a medical image deployed upon designation of the medical image display command icon I1 shown in FIG. 10. When an SC image display command icon concerning series 2 is designated, the control circuitry 11 deploys a plurality of SC images generated as a result of executing processing task "MPR" with respect to a medical image deployed upon designation of the medical image display command icon I2 shown in FIG. 10. When an SC image display command icon concerning series 3 is designated, the control circuitry 11 deploys a plurality of capture images generated as a result of executing processing task "MPR" with respect to a medical image deployed upon designation of the medical image display command icon I3 shown in FIG. 10.

As shown in FIG. 10, with regard to processing task "large intestine analysis" corresponding to state information "unexecuted", for example, the control circuitry 11 causes the display 12 to display an image processing state display icon I5 associated with a program for generating an instruction to execute a predetermined processing task. The image processing state display icon I5 displays processing task name "large intestine analysis" to allow recognition of processing task "large intestine analysis" as being "unexecuted", as shown in FIG. 10.

When the image processing state display icon I5 is designated, for example, the control circuitry 11 generates an instruction to execute an execution program for processing task "large intestine analysis" to be executed for a medical image deployed upon designation of a medical image display command icon.

An execution program for processing task "large intestine analysis" is, for example, set to be executed for medical images contained in medical image files belonging to all series concerning an examination to which a display request is issued. That is, an execution program for processing task "large intestine analysis" is set to be executed for medical images contained in medical image files belonging to series 1 associated with the medical image display command icon I1, medical images contained in medical image files belonging to series 2 associated with the medical image display command icon I2, and medical images contained in medical image files belonging to series 3 associated with the medical image display command icon I3, which are shown in, for example, FIG. 10.

Note that an execution program for processing task "large intestine analysis" may be set to be executed for medical images contained in medical image files belonging to each series.

Upon receiving an image list display request, the control circuitry 11 monitors whether a processing task requested by, for example, an examination technician is executed in the examination while an image list requested to be displayed is displayed. When, for example, an SC image file necessary for a requested examination is output to the image archiving server 30, the control circuitry 11 determines that a processing task necessary for the requested examination has been executed, and updates the state information of the processing task to "executed" in the task management table 152. When the state information of a record registered in the task management table 152 is updated, the control circuitry 11 executes the display control function 113 to update the display screen displayed on the display 12.

Figure 11:
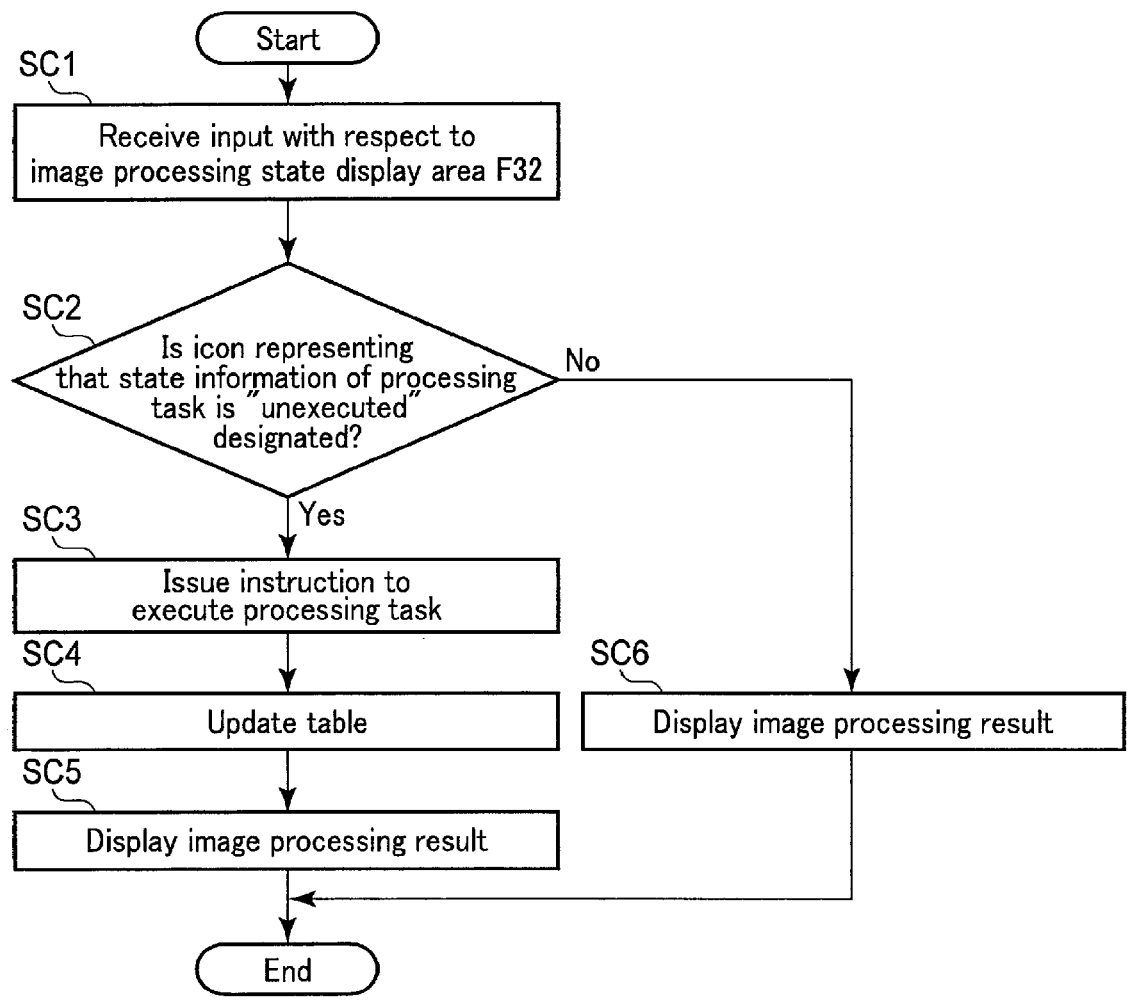
FIG. 11 is a flowchart showing a procedure for processing to be performed upon designation of a predetermined image processing state display icon displayed on the display according to the first embodiment.

A procedure for executing a processing task upon designation of an image processing state display icon displayed on the display 12 according to the first embodiment will be described with reference to FIGS. 10 and 11. FIG. 11 is a flowchart showing an example of a procedure for processing to be performed when a predetermined image processing state display icon displayed on the display 12 according to the first embodiment is designated.

First of all, the control circuitry 11 stands by until an arbitrary position in the image processing state display area F32 shown in FIG. 11 is touched via the input interface 13 (step SC1).

When an arbitrary position in the image processing state display area F32 is touched, the control circuitry 11 determines whether the touched position corresponds to an image processing state display icon representing that the corresponding processing task has not been executed, that is, the state information is "unexecuted" (step SC2).

If the touched position on the image processing state display area F32 corresponds to the image processing state display icon representing that the corresponding processing task has not been executed (YES in step SC2), the control circuitry 11 executes the task execution instruction function 114 (SC3). The control circuitry 11 executes the task execution instruction function 114 to generate an instruction to execute the processing task associated with the image processing state display icon. The control circuitry 11 transfers the generated execution instruction to, for example, the workstation 20 via the communication interface 14.

When, for example, the image processing state display icon I5 shown in FIG. 10 is designated, the control circuitry 11 transfers an instruction to execute processing task "large intestine analysis" to the workstation 20 via the communication interface 14. With this operation, the control circuitry 23 of the workstation 20 generates a capture image by executing processing task "large intestine analysis".

The workstation 20 generates an SC image file by converting the generated capture image into a format, for example, complying with the DICOM standard. The workstation 20 then transmits an execution result containing information indicating "executed" to the medical image display apparatus 10 via the communication interface 21. The workstation 20 transmits the generated SC image file to the image archiving server 30.

Upon receiving the execution result containing information indicating "executed" from the workstation 20, the medical image display apparatus 10 acquires the SC image file transmitted from the workstation 20 to the image archiving server 30 from the image archiving server 30. Note that the medical image display apparatus 10 may check the presence/absence of an execution result by, for example, polling the workstation 20 at predetermined intervals. In addition, the execution result containing information indicating "executed" may be transmitted to the image archiving server 30. At this time, the medical image display apparatus 10 checks the presence/absence of an execution result by, for example, polling the image archiving server 30 at predetermined intervals.

Upon acquiring an SC image file generated in accordance with an execution instruction from the image archiving server 30, the control circuitry 11 executes the task management function 115 to update the state information of the processing task to "executed" in the task management table 152 (step SC4). For example, the control circuitry 11 updates the state information of processing task "large intestine analysis" from "unexecuted" to "executed".

The control circuitry 11 executes the display control function 113 upon updating the state information of the processing task to "executed" in the task management table 152. The control circuitry 11 executes the display control function 113 to refer to the task management table 152 so as to generate image data representing that the state information of processing task "large intestine analysis" is "executed". The control circuitry 11 controls the display 12 to display the generated image data as an image processing state display icon in the image list display area F3 shown in, for example, FIG. 10 together with an image list concerning the medical image file (step SC5).

The control circuitry 11 executes the display control function 113 (step SC6) if a touched position on the image processing state display area F3 is not a position corresponding to an image processing state display icon representing "unexecuted", that is, is a position corresponding to an image processing state display icon representing that a predetermined processing task has been executed (NO in step SC2). The control circuitry 11 executes the display control function 113 to, for example, display a capture image as a result of executing a processing task. When, for example, the image processing state display icon I4 shown in FIG. 10 is designated, the control circuitry 11 displays an MPR image as a result of executing processing task "MPR".

As described above, according to the first embodiment, the control circuitry 11 provided in the medical image display apparatus 10 specifies a necessary processing task by collating clinical keywords stored in the task correspondence table 151 with examination reservation information requesting the execution of an examination. The control circuitry 11 registers the specified processing task in the task management table 152. The control circuitry 11 determines, in accordance with a medical image display request, whether the processing task specified concerning the requested medical image, registered in the task management table 152, has been executed. The control circuitry 11 updates the state information of the processing task in the task management table 152 based on the result of determining whether the processing task has been executed. This enables the control circuitry 11 to grasp whether the processing task has been executed.

The medical image display apparatus 10 according to this embodiment can therefore prevent the omission of execution of image processing.

According to the first embodiment, the control circuitry 11 refers to the task management table 152 to display a thumbnail of a capture image generated as a result of executing the processing task and the processing task name, if the state information of the processing task is "executed". The control circuitry 11 refers to the task management table 152 to display an image processing state display icon displaying, for example, only a processing task name, if the state information of the processing task is "unexecuted". This allows an interpretation doctor or the like to recognize whether a processing task exists and the processing task has been executed. This also makes it possible to clearly indicate that a processing task to be executed has not been executed.

According to the first embodiment, the control circuitry 11 displays the image processing state display icons 14 and 15 representing whether a processing task has been executed in the image list display area F3 displaying the medical image display command icons I1, I2, and I3 for deploying medical images as radiographic interpretation targets. When performing radiographic interpretation, the interpretation doctor closely examines an image necessary for radiographic interpretation by, for example, referring to the image list display area F3. According to the first embodiment, because the image processing state display icons I4 and I5 are displayed in the image list display area F3, to which the interpretation doctor refers when performing radiographic interpretation, the interpretation doctor can notice that predetermined image processing has not been executed without deviating from a conventional radiographic interpretation procedure. That is, it is possible to prevent the omission of execution of image processing.

According to the first embodiment, the control circuitry 11 manages processing tasks by associating them with order numbers concerning requested examinations in the task management table 152. On the other hand, additional information in a medical image file generated by executing a requested examination includes an order number. This enables the control circuitry 11 to reliably execute a processing task requested to be executed for a medical image acquired by executing a requested examination. That is, the interpretation doctor can reliably execute a processing task requested to be executed by designating a predetermined image processing state display icon without making any selection mistake when executing a processing task that has not been executed.

According to the first embodiment, upon receiving an image list display request, the control circuitry 11 monitors whether a processing task requested by, for example, an examination technician to be executed in an examination has been executed, while displaying an image list requested to be displayed. When, for example, an SC image file necessary for a requested examination is output to the image archiving server 30, while an image list requested to be displayed is displayed, the control circuitry 11 determines that a processing task necessary for the requested examination has been executed. The control circuitry 11 updates the state information of the processing task to "executed" in the task management table 152. Upon updating the state information of a record registered in the task management table 152, the control circuitry 11 updates a display screen to be displayed on the display 12.

After an interpretation doctor starts radiographic interpretation, an examination technician sometimes notices the omission of execution of a processing task. In this case, even when the examination technician, who has noticed the omission of execution of the processing task, executes the necessary processing task, the interpretation doctor or the like may not notice a capture image and the like generated as a result of executing the processing task. According to the first embodiment, it is possible to prevent an interpretation doctor from failing to notice a capture image and the like generated by an examination technician after the start of radiographic interpretation.

According to the first embodiment, for example, while executing a processing task for which an execution instruction has been issued, the control circuitry 11 may superimpose an identifier indicating that the processing task is being executed on an image processing state display icon. An identifier indicating that the processing task is being executed is represented by, for example, a progress bar, sandglass, ring cursor (busy cursor), or character. In this case, when the execution of the processing task is instructed by designating an image processing state display icon, the control circuitry 11 generates execution instruction information for instructing the execution of the instructed processing task. The control circuitry 11 transfers the generated execution instruction information to, for example, the workstation 20 via the communication interface 14. Upon transferring the execution instruction information, the control circuitry 11 superimposes, for example, an identifier indicating that the processing task for which an execution instruction has been issued is being executed on an image processing state display icon. Upon receiving an execution result containing information indicating "executed" with respect to a processing task for which an execution instruction has been issued from, for example, the workstation 20, the control circuitry 11 finishes displaying an identifier indicating that the processing task is being executed. Note that an identifier indicating that the processing task is being executed may be displayed parallel with an image processing state display icon. In addition, an identifier indicating that the processing task is being executed may be displayed in place of an image processing state display icon.

Second Embodiment

The first embodiment has exemplified the case in which processing tasks are managed in an image display apparatus which does not archive any medical image files and SC image files. The second embodiment will exemplify a case in which processing tasks are managed in an image archiving server which archives medical image files and SC image files.

FIG. 12 is a schematic view showing a medical information system including an image archiving server 30A according to the second embodiment. The medical information system shown in FIG. 12 includes the image archiving server 30A, a viewer 10A, a workstation 20, an HIS server, an RIS server 41, an RIS terminal 42, and a medical image diagnostic apparatus 50. The image archiving server 30A, the viewer 10A, the workstation 20, the HIS server, the RIS server 41, the RIS terminal 42, and the medical image diagnostic apparatus 50 are connected to a local network to transmit information to predetermined apparatuses and receive information transmitted from predetermined apparatuses. Note that the medical information system may be connected to an external network in addition to or in place of the local network.

Referring to FIG. 12, the image archiving server 30A, the viewer 10A, and the workstation 20 are some of the elements constituting a PACS (Picture Archiving and Communication System). The RIS server 41 and the RIS terminal 42 are some of the elements constituting an RIS (Radiology Information System).

The function of the RIS server 41 is the same as that of the RIS server 41 according to the above embodiment. The function of the medical image diagnostic apparatus 50 is the same as that of the medical image diagnostic apparatus 50 according to the above embodiment. The medical image diagnostic apparatus 50 outputs generated medical image files to the image archiving server 30A and the workstation 20.

The function of the workstation 20 is the same as that of the workstation 20 according to the above embodiment.

The image archiving server 30A archives a medical image file output from the medical image diagnostic apparatus 50 in a predetermined storage device of the image archiving server 30A, and outputs an archived medical image file in accordance with a request.

The viewer 10A and the image archiving server 30A will be described in detail below.

Figure 13:
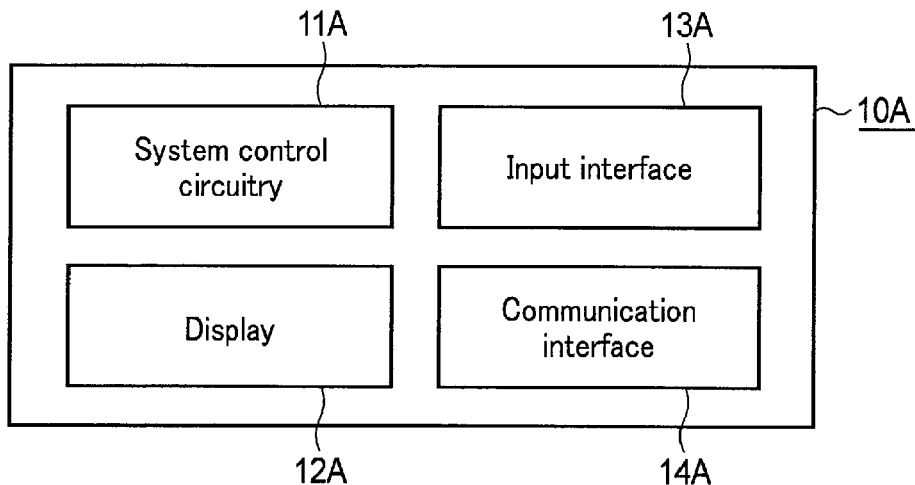
FIG. 13 is a block diagram showing the arrangement of a viewer according to the second embodiment.

The viewer 10A according to the second embodiment assumes, for example, the role of a DICOM viewer. FIG. 13 is a block diagram showing an example of the arrangement of the viewer 10A according to the second embodiment. The viewer 10A shown in FIG. 13 includes system control circuitry 11A, a display 12A, an input interface 13A, and a communication interface 14A. The system control circuitry 11A, the display 12A, the input interface 13A, and the communication interface 14A are communicably connected to each other via, for example, a bus.

The system control circuitry 11A is a processor for controlling, for example, each constituent circuitry of the viewer 10A. The system control circuitry 11A functions as the main unit of the viewer 10A. More specifically, the system control circuitry 11A controls the display 12A to display medical images based on medical image files and capture images based on SC image files which are transmitted from the image archiving server 30A. In addition, the system control circuitry 11A receives medical image files and SC image files from the image archiving server 30A via the communication interface 14A.

The display 12A has a general display output device such as a liquid crystal display or OLED (Organic Light Emitting Diode) display. The display 12A displays, for example, medical images based on medical image files and capture images based on SC image files, which are transmitted from the image archiving server 30A, under the control of the system control circuitry 11A.

The input interface 13A is implemented by, for example, a mouse, a keyboard, and a touch pad having an operation screen that the operator touches to input an instruction. The input interface 13A receives various types of instructions from the operator. The input interface 13A receives an image list display request from, for example, an interpretation doctor. The input interface 13A is connected to the system control circuitry 11A via, for example, a bus. The input interface 13A converts an operation instruction input from the operator into an electrical signal and outputs it to the system control circuitry 11A.

The communication interface 14A communicates data with external apparatuses such as the workstation 20 and the image archiving server 30A, to which the communication interface 14A is connected via the network shown in FIG. 12 or the like.

Figure 14:
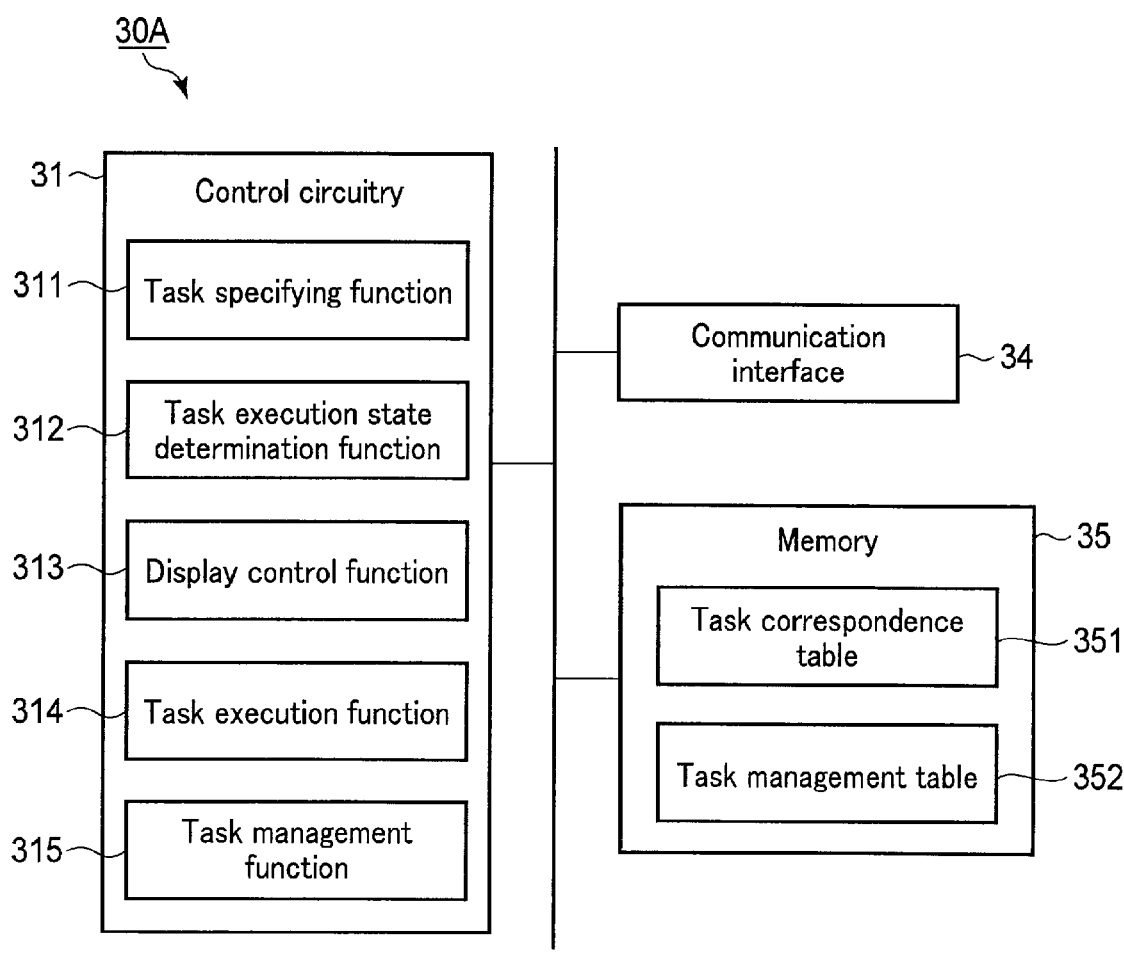
FIG. 14 is a block diagram showing the arrangement of an image archiving server according to the second embodiment.

The image archiving server 30A according to the second embodiment assumes, for example, the role of a DICOM server. FIG. 14 is a block diagram showing an example of the arrangement of the image archiving server 30A according to the second embodiment. The image archiving server 30A shown in FIG. 14 includes control circuitry 31, a communication interface 34, and a memory 35. The control circuitry 31, the communication interface 34, and the memory 35 are communicably connected to each other via, for example, a bus.

The control circuitry 31 is a processor functioning as the main unit of the image archiving server 30A. The control circuitry 31 executes processing tasks stored in the memory 35 or the like to implement functions corresponding to the programs.

The communication interface 34 communicates data with external apparatuses such as the workstation 20, the viewer 10A, the RIS server 41 of the radiology information system, and the medical image diagnostic apparatus 50, to which the communication interface 34 is connected via the network shown in FIG. 12 or the like.

The arrangement of the memory 35 is the same as that of the memory 15 according to the above embodiment. The memory 35 stores a task correspondence table 351 and a task management table 352. The functions of the task correspondence table 351 and the task management table 352 are the same as those of the task correspondence table 151 and the task management table 152 according to the first embodiment. The memory 35 stores medical image files and SC image files output from the medical image diagnostic apparatus 50. The memory 35 also stores image processing programs for executing various types of processing tasks. In addition, the memory 35 stores a task execution count, execution date, and execution user as additional information of a processing task concerning a predetermined examination.

The control circuitry 31 according to the second embodiment implements various functions shown in FIG. 13 by executing operation programs read out from the memory 35. That is, the control circuitry 31 includes a task specifying function 311, a task execution state determination function 312, a display control function 313, a task execution function 314, and a task management function 315.

The role of the task specifying function 311 is the same as that of the task specifying function 111 according to the first embodiment.

The task execution state determination function 312 is a function for determining whether the processing task specified by the execution of the task specifying function 311 has been executed. When the task execution state determination function 312 is executed, the control circuitry 31 determines, based on additional information in a medical image file and additional information in an SC image file, whether the processing task specified by the execution of the task specifying function 311 has been executed.

The display control function 313 is a function for controlling the communication interface 34 to transmit, to the viewer 10A, image data representing whether a processing task has been executed. Upon executing the display control function 313, when a necessary processing task is specified by the execution of the task specifying function 311, the control circuitry 31 generates image data representing whether the processing task has been executed, in accordance with a determination result indicating whether the specified processing task has been executed. The control circuitry 31 controls the communication interface 34 to transmit the generated image data to the viewer 10A together with the additional information of the processing task concerning the image data.

The task execution function 314 is a function for executing, based on an instruction to execute a processing task, the processing task for which the execution instruction has been issued. Upon executing the task execution function 314, the control circuitry 31 reads out an image processing program corresponding to the instruction to execute the processing task transmitted from the viewer 10A from the memory 35 via the communication interface 34. The control circuitry 31 executes the read image processing program to execute the processing task designated via the input interface 13A, thereby generating a capture image. The control circuitry 31 generates an SC image file by converting the generated capture image into a format complying with, for example, the DICOM standard.

The role of the task management function 315 is the same as that of the task management function 115 according to the first embodiment.

Figure 15:
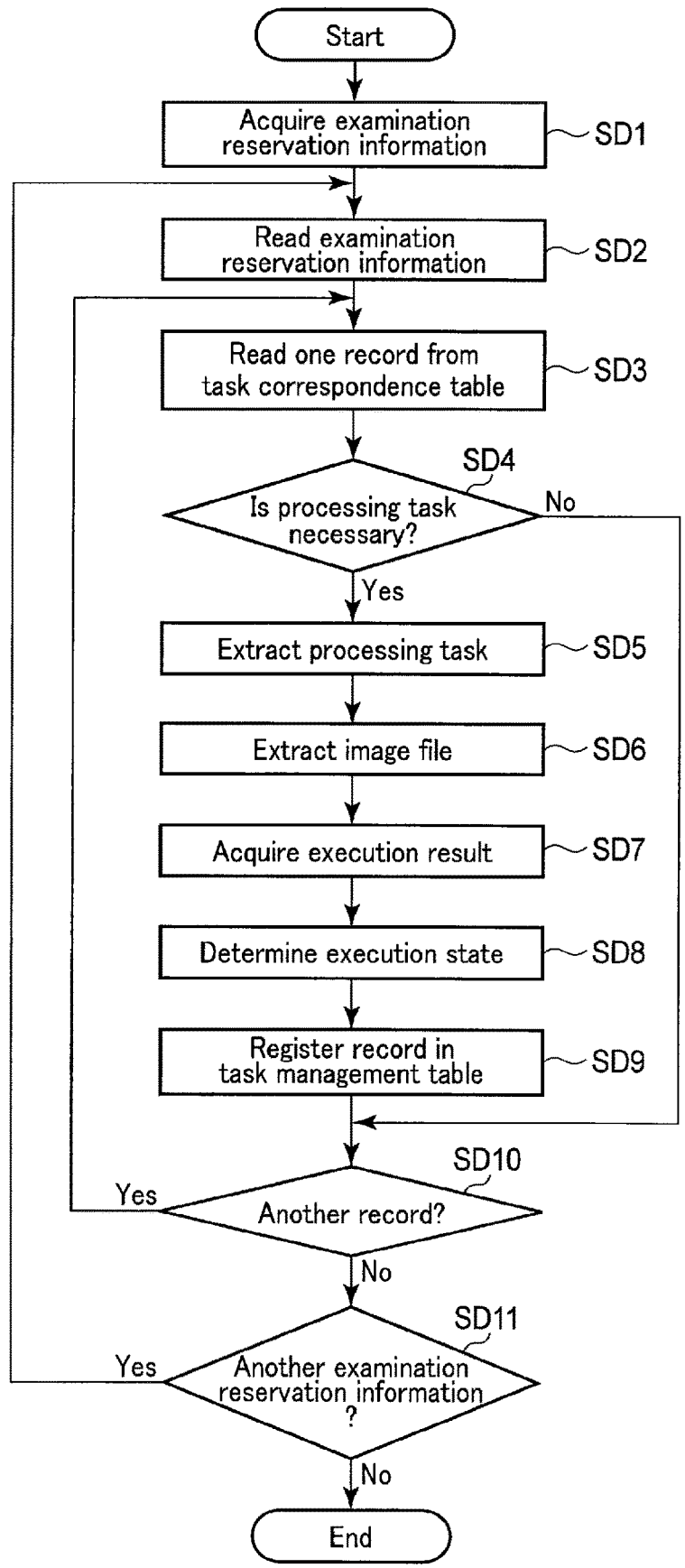
FIG. 15 is a flowchart showing a procedure in which control circuitry according to the second embodiment specifies a processing task, and determines whether the specified processing task has been executed.

An operation in which the image archiving server 30A having the above arrangement specifies a processing task will be described. FIG. 15 is a flowchart showing an example of a procedure in which the control circuitry 31 according to the second embodiment specifies a processing task and determines whether the specified processing task has been executed.

Upon receiving an activation instruction to activate a predetermined application for displaying a medical image and a capture image from the viewer 10A via the communication interface 34, the control circuitry 31 executes the task specifying function 311. The control circuitry 31 executes the task specifying function 311 to acquire examination reservation information from the RIS server 41 (step SD1).

The control circuitry 31 reads one piece of the acquired examination reservation information (step SD2). Assume that in this case, the read examination reservation information contains order number "000001", patient ID "00001", apparatus "X-ray CT examination", procedure "CT colonography", imaging region "large intestine", body posture "none specified", and imaging direction "none specified".

Upon reading examination reservation information in step SD2, the control circuitry 31 reads one record from the task correspondence table 351 shown in FIG. 5 (step SD3).

The control circuitry 31 determines, for example, whether processing task "large intestine analysis" set in the record read in step SD3 is necessary for the examination reservation information read in step SD2 (step SD4).

Because clinical keyword "CT, large intestine, colonography" is contained in the character string contained in the examination reservation information, the control circuitry 31 determines that the processing task is necessary for the examination reservation information (YES in step SD4). The control circuitry 31 then extracts processing task "large intestine analysis" associated with the clinical keyword from the task correspondence table 351 (step SD5).

The control circuitry 31 extracts medical image files and SC image files, each containing order number "000001" contained in the examination reservation information read in step SD2, from the medical image files and SC image files stored in the memory 35 by using order number "000001" as a key (step SD6).

The control circuitry 31 refers to additional information in the medical image files and SC image files extracted in step SD6 to acquire an execution result of processing task "large intestine analysis" extracted in step SD5, that is, the number of SC image files, of the SC image files corresponding to order number "000001", in which information capable of specifying the processing task contained in the additional information represents processing task "large intestine analysis" (step SD7).

The control circuitry 31 compares the number of SC image files acquired in step SD7 with a number set in advance for each processing task to determine whether the processing task has been executed (step SD8).

Upon determining whether the processing task has been executed, the control circuitry 31 executes the task management function 315. The control circuitry 31 executes the task management function 315 to register a record concerning extracted processing task "large intestine analysis" in the task management table 352 shown in FIG. 6 (step SD9). That is, the control circuitry 31 registers a record containing order number "000001", processing task "large intestine analysis", and state information "unexecuted" in the task management table 352.

The control circuitry 31 determines whether the records registered in the task correspondence table 351 include another record for which the necessity to execute the processing task has not been determined (step SD10).

If there is another record for which the necessity to execute the processing task has not been determined (YES in step SD10), the control circuitry 31 reads one record for which the necessity to execute the processing task has not been determined from task correspondence table 351 (step SD3), and executes the processing from step SD4 to step SD9 again.

If there is not another record for which the necessity to execute the processing task has not been determined (NO in step SD10), the control circuitry 11 determines whether there is another examination reservation information for which the necessity of a processing task has not been determined (step SD11).

If there is another examination reservation information for which the necessity of a processing task has not been determined (YES in step SD11), the control circuitry 31 reads one piece of examination reservation information (step SD2), and executes the processing from step SD3 to step SD10 again.

If there is not another examination reservation information for which the necessity of a processing task has not been determined (NO in step SD11), the control circuitry 31 finishes processing by the task specifying function 311.

The next will describe an operation in which the image archiving server 30A acquires the state information of a processing task registered in the task management table 352 and displays a predetermined image representing the acquired state information on the display 12A. FIG. 16 is a flowchart showing a procedure in which the control circuitry 31 according to the second embodiment transmits image data representing whether a processing task has been executed to the viewer 10A in accordance with an image list display request.

Assume that an image list display request is issued by, for example, designating a patient ID and an examination UID as in the first embodiment. At this time, for example, a display screen like that shown in FIG. 8 is displayed on the display 12A of the viewer 10A. Assume also that an interpretation doctor or the like inputs an image list display request via the input interface 13A of the viewer 10A. The input image list display request is transmitted to the image archiving server 30A via the communication interface 14A of the viewer 10A.

The control circuitry 31 receives an image list display request transmitted from the viewer 10A via the communication interface 34 (step SE1).

As shown in, for example, FIG. 8, upon receiving an image list display request concerning the examination executed "at 7 a.m. on Mar. 4, 2016" with respect to a patient corresponding to patient ID "00001", the control circuitry 31 extracts a medical image file and an SC image file containing the examination UID assigned to this examination, for example, "0001", from the medical image file and the SC image file stored in the memory 35 (step SE2).

The control circuitry 31 acquires the order number contained in additional information in the extracted medical image file or SC image file, for example, "000001" (step SE3).

The control circuitry 31 determines whether a record corresponding to acquired order number "000001" exists in the task management table 352 (step SE4).

If a record corresponding to acquired order number "000001" does not exist in the task management table 352 (NO in step SE4), the control circuitry 31 executes the display control function 313. The control circuitry 31 executes the display control function 313 to control the communication interface 34 to transmit image data representing an image list concerning the medical image file extracted in step SE2 to the viewer 10A (step SE6). The display 12A of the viewer 10A displays the image data representing the image list concerning the medical image file transmitted to the viewer 10A in the image list display area F3 shown in, for example, FIG. 8.

If a record corresponding to acquired order number "000001" exists in the task management table 352 (YES in step SE4), the control circuitry 31 executes the display control function 313. The control circuitry 31 executes the display control function 313 to refer to the task management table 352 shown in FIG. 9 so as to generate, for, for example, each series, image data representing whether a processing task corresponding to order number "000001" linked to examination UID "0001" assigned to the examination designated in an image list display request has been executed, in accordance with the value of the state information of the processing task. The control circuitry 31 controls the communication interface 34 to transmit the generated image data to the viewer 10A together with the image data representing the image list concerning the medical image file (step SE5). The display 12A of the viewer 10A displays, in the image list display area F3 shown in FIG. 8, the image data representing whether the processing task transmitted to the viewer 10A has been executed and the image data representing the image list concerning medical image file.

Figure 17:
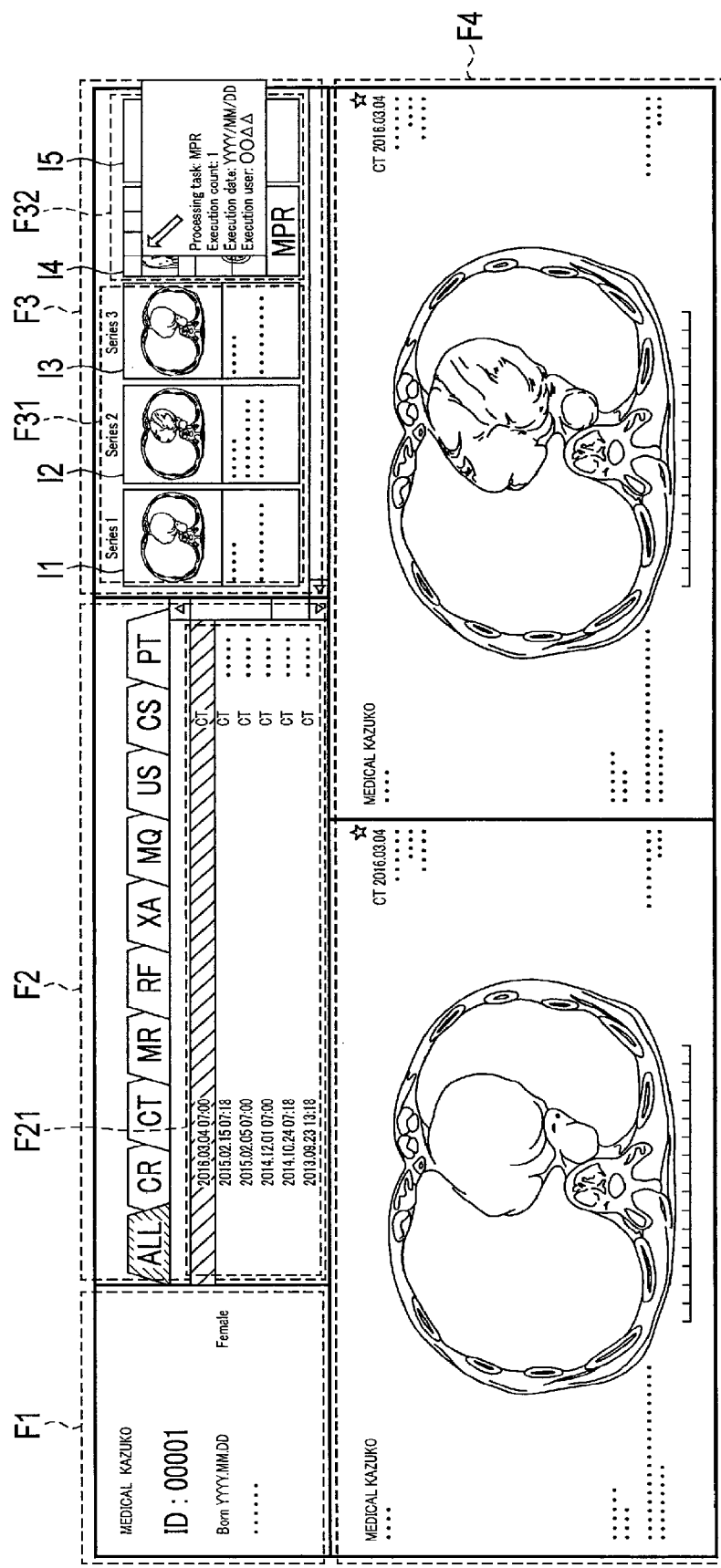
FIG. 17 is a view showing a balloon displayed on the display of the viewer according to the second embodiment.

Note that when, for example, a predetermined cursor is set on an image processing state display icon via the mouse of the input interface 13A, the system control circuitry 11A of the viewer 10A displays, in a sub-screen, a task execution count, execution date, and execution user concerning a processing task executed at the time of generating a secondary capture linked to the icon. FIG. 17 is a view showing an example of a sub-screen displayed on the display 12A of the viewer 10A according to the second embodiment. As shown in FIG. 17, for example, when the cursor of the mouse is set on the image processing state display icon I4, a task execution count, execution date, and execution user concerning processing task "MPR" are displayed in a sub-screen.

Figure 18:
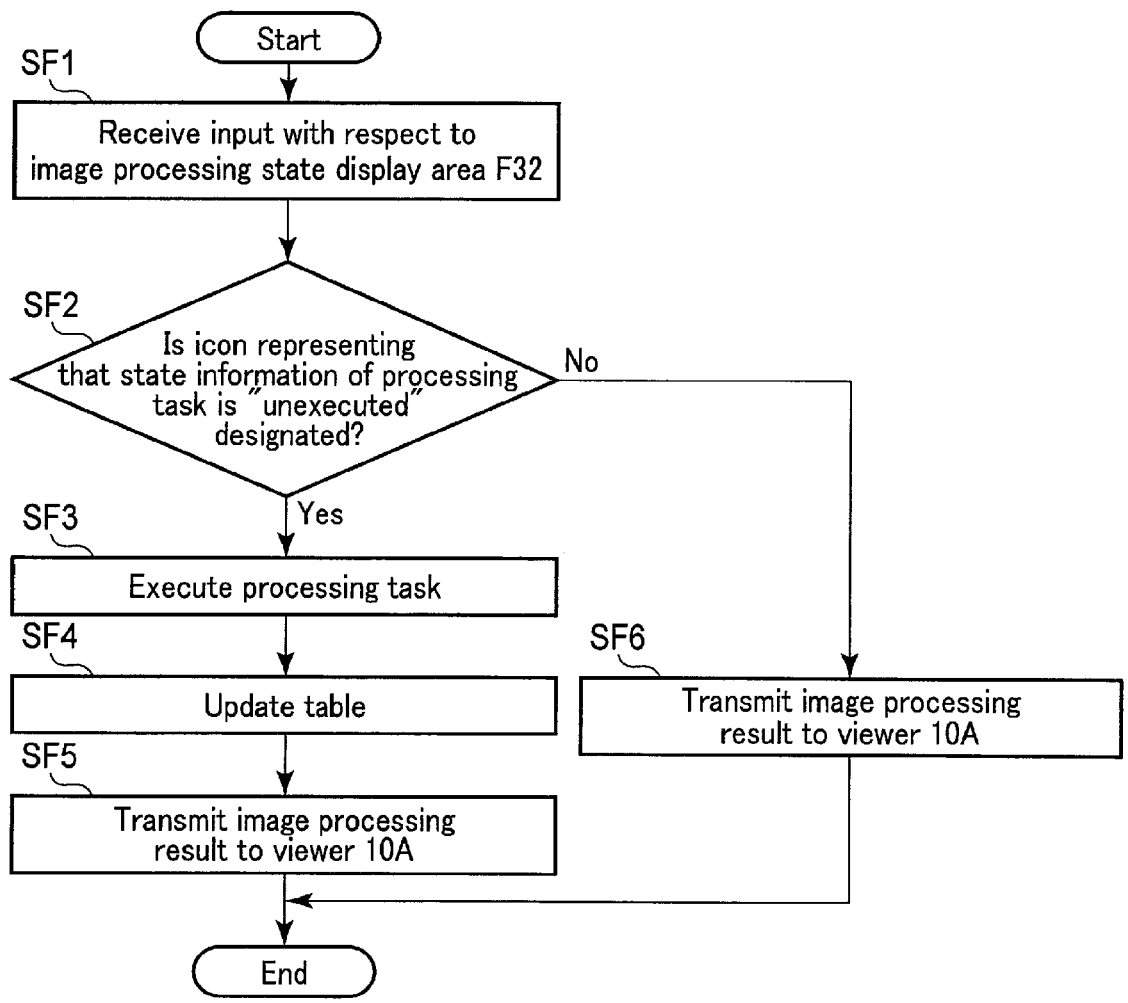
FIG. 18 is a flowchart showing a procedure for processing to be performed upon designation of a predetermined image processing state display icon displayed on the display of the viewer according to the first embodiment.

A procedure for executing a processing task via the image list displayed on the display 12A according to the second embodiment will be described next with reference to FIG. 18. FIG. 18 is a flowchart showing an example of a procedure for processing when a predetermined image processing state display icon displayed on the display 12A of the viewer 10A according to the second embodiment is designated.

First of all, the control circuitry 31 stands by until a touch on an arbitrary position in the image processing state display area F32 is notified from the viewer 10A via the communication interface 34 (step SF1).

When a touch on an arbitrary position in the image processing state display area F32 is notified from the viewer 10A, the control circuitry 31 determines whether the touched position is a position corresponding to an image processing state display icon representing that the processing task has not been executed (step SF2).

If the position designated in step SD2 is a position corresponding to an image processing state display icon representing that a processing task has not been executed (YES in step SF2), the control circuitry 31 executes the task execution function 314 (step SF3). The control circuitry 31 executes the task execution function 314 to read out an image processing program concerning the processing task associated with the image processing state display icon from the memory 35. The control circuitry 31 executes the read image processing program. When, for example, the image processing state display icon I5 shown in FIG. 10 is designated, the control circuitry 31 reads out an image processing program concerning processing task "large intestine analysis" from the memory 35. The control circuitry 31 generates a capture image by executing the readout image processing program concerning processing task "large intestine analysis". The control circuitry 31 generates an SC image file by converting the generated capture image into a format complying with, for example, the DICOM standard. The control circuitry 31 then acquires an execution result containing information indicating "executed".

Upon acquiring the execution result containing the information indicating "executed", the control circuitry 31 executes the task management function 315 to update the state information of the processing task to "executed" in the task management table 352 (step SF4). The control circuitry 31 updates, for example, the state information of processing task "large intestine analysis" from "unexecuted" to "executed".

Upon updating the state information of the processing task to "executed" in the task management table 352, the control circuitry 31 executes the display control function 313. The control circuitry 31 executes the display control function 313 to refer to the task management table 352 so as to generate image data representing that processing task "large intestine analysis" has been executed. The control circuitry 31 controls the communication interface 34 to transmit the generated imaged data to the viewer 10A (step SF5).

The control circuitry 31 executes the display control function 313 (step SF6) if a touched position on the image processing state display area F3 is not a position corresponding to an image processing state display icon representing that the processing task has not been executed, that is, a position corresponding to an image processing state display icon representing that a predetermined processing task has been executed (NO in step SF2). The control circuitry 31 executes the display control function 313 to transmit, for example, a capture image as an execution result of the processing task to the viewer 10A via the communication interface 34. The system control circuitry 11A of the viewer 10A controls the display 12A to display a received capture image.

When the image processing state display icon I4 representing that processing task "MPR" has been executed is designated on the display 12A of the viewer 10A, the control circuitry 31 transmits MPR image data representing an MPR image as an execution result of processing task "MPR" concerning the designated examination to the viewer 10A via the communication interface 34. The system control circuitry 11A of the viewer 10A controls the display 12A to display an MPR image based on the received MPR image data.

As described above, according to the second embodiment, the memory 35 of the image archiving server 30A stores medical image files and SC image files output from the medical image diagnostic apparatus 50. This makes it possible to eliminate the necessity to read out medical image files and SC image files via a network, thereby reducing the communication load.

According to the second embodiment, upon executing the task execution function 314, the control circuitry 31 of the image archiving server 30A executes a processing task. This eliminates the necessity to acquire SC image files and execution results such as measurement values via a network, and hence can reduce the communication load and shorten the time from the instant the execution of a processing task is requested to the instant the execution result is acquired.

According to the second embodiment, for example, while a processing task for which an execution instruction has been issued is executed, the control circuitry 31 may superimpose an identifier indicating that the processing task is being executed on an image processing state display icon on the display 12A of the viewer 10A. At this time, when an execution instruction is issued for the processing task by designating an image processing state display icon, the control circuitry 31 starts executing the designated processing task. Upon starting the designated processing task, for example, the control circuitry 31 generates, for example, display instruction information for instructing to superimpose an identifier indicating that the designated processing task is being executed on an image processing state display icon. The control circuitry 31 transmits, for example, generated display instruction information to the viewer 10A via the communication interface 34. The system control circuitry 11A of the viewer 10A then controls the display 12A to superimpose the identifier indicating that a processing task for which an execution instruction is issued on an image processing state display icon based on the display instruction information.

The control circuitry 31 then transmits the execution result generated by the execution of the processing task to the viewer 10A via the communication interface 34. The system control circuitry 11A of the viewer 10A controls the display 12A to finish displaying the identifier indicating that the processing task is being executed. Note that the identifier indicating that the processing task is being executed may be displayed parallel with an image processing state display icon. Alternatively, the identifier indicating that the processing task is being executed may be displayed in place of an image processing state display icon.

[Modification]

The first and second embodiments each have exemplified the case in which additional information in a medical image file and additional information in an SC image file each include an order number. However, in some case, additional information in a medical image file and additional information in an SC image file each include no order number. The following will describe a case in which additional information in a medical image file and additional information in an SC image file each include no order number.

This modification will be described with reference to the arrangement of the medical information system according to the first embodiment. That is, the following will describe a case in which the medical image display apparatus 10 shown in FIG. 2 executes various types of functions for managing execution/non-execution of processing tasks such as the task specifying function, the task execution state determination function, and the task management function. Note that this modification may be applied to the arrangement of the medical information system according to the second embodiment. That is, for example, the image archiving server 30A shown in FIG. 14 may be applied to the arrangement of a medical information system configured to execute various types of functions for managing execution/non-execution of processing tasks such as the task specifying function, the task execution state determination function, and the task management function.

Figure 19:
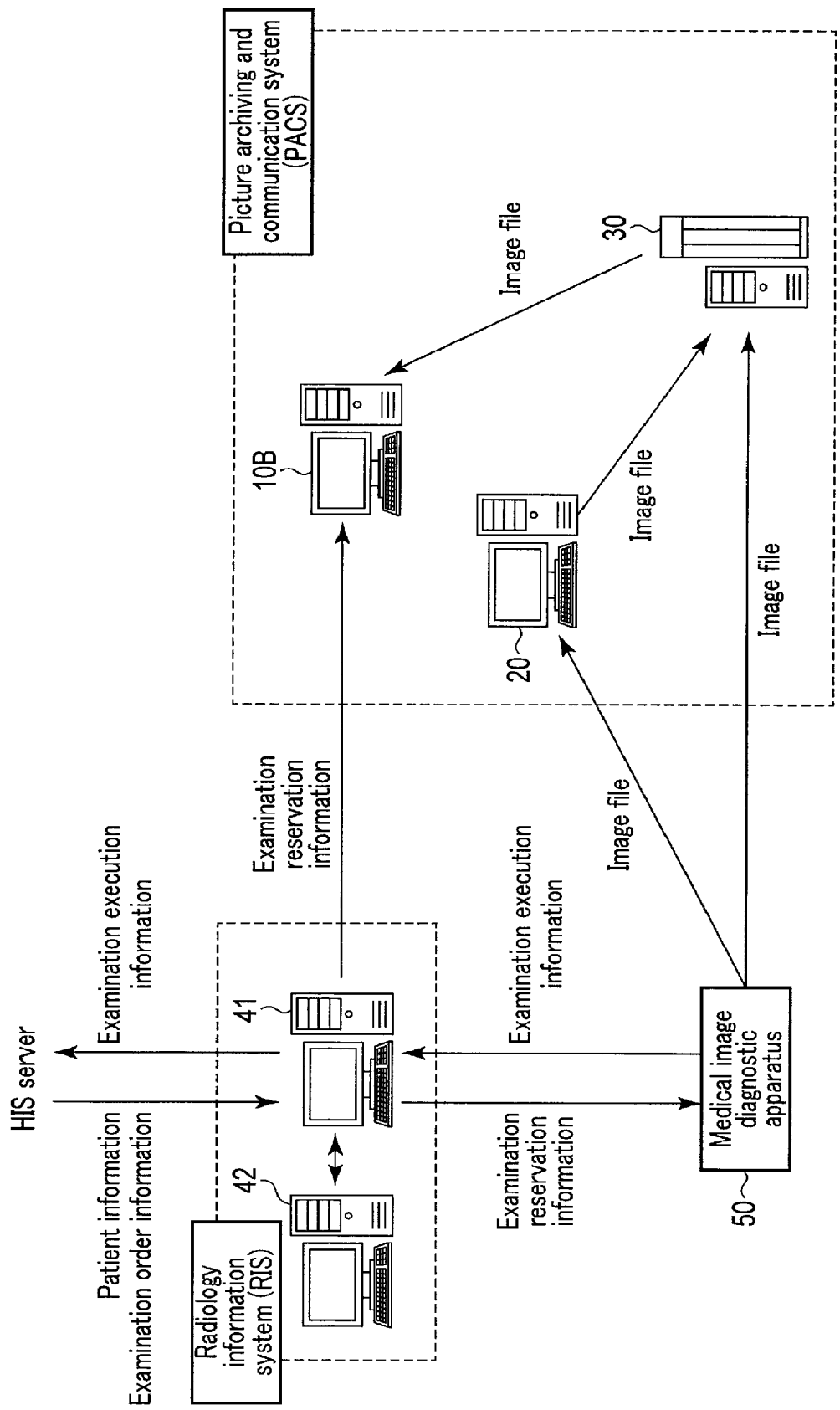
FIG. 19 is a schematic view showing a medical information system including a medical image display apparatus according to a modification.

FIG. 19 is a schematic view showing a medical information system including a medical image display apparatus 10B according to the modification. The medical information system shown in FIG. 19 includes the medical image display apparatus 10B, the workstation 20, the image archiving server 30, the HIS server, the RIS server 41, the RIS terminal 42, and the medical image diagnostic apparatus 50.

The medical image display apparatus 10B will be described in detail below.

The medical image display apparatus 10B according to the modification assumes, for example, the role of a DICOM viewer. FIG. 20 is a block diagram showing an example of the arrangement of the medical image display apparatus 10B according to the modification. The medical image display apparatus 10B shown in FIG. 20 includes control circuitry 11B, the display 12, the input interface 13, the communication interface 14, and a memory 15B. The control circuitry 11B, the display 12, the input interface 13, the communication interface 14, and the memory 15B are communicably connected to each other via, for example, a bus.

The control circuitry 11B is a processor functioning as the main unit of the medical image display apparatus 10B. The control circuitry 11B executes various operation programs stored in the memory 15B or the like to implement functions corresponding to the programs.

The memory 15B is a storage device such as an HDD, SSD, or integrated circuitry storage device that stores various types of information. The memory 15B stores the task correspondence table 151 and a task management table 152B.

The task management table 152B is a table that associates each "processing task" to be executed for a requested examination with "state information" representing whether the "processing task" has been executed, and is a table for managing whether each processing task has been executed.

Each record in the task management table 152B is registered with, for example, an examination UID as a key.

The control circuitry 11B according to the modification implements various functions shown in FIG. 20 by executing operation programs read out from the memory 15B. That is, the control circuitry 11B includes the task specifying function 111, a task execution state determination function 112B, the display control function 113, the task execution instruction function 114, and a task management function 115B.

The task execution state determination function 112B is a function for determining whether a processing task specified by the execution of the task specifying function 111 has been executed. When the task execution state determination function 112B is executed, the control circuitry 11 determines, based on additional information in a medical image file and additional information in an SC image file, whether a processing task registered in the task management table 152B has been executed.

In this modification, additional information in a medical image file includes, for example, information for specifying a medical image, such as an examination UID, series UID, patient ID, modality code, series NO., and series description corresponding to a generated medical image. Additional information in an SC image file includes, for example, information for specifying a medical image, such as an examination UID, series UID, patient ID, modality code, series NO., and series description corresponding to a generated capture image.

The task management function 115B is a function for managing records in the task management table 152B. In this modification, when the task management function 115B is executed, the control circuitry 11B registers a record concerning a processing task specified by the task specifying function 111 with, for example, an examination UID as a key, and updates the state information of the processing task concerning the registered record.

Figure 21:
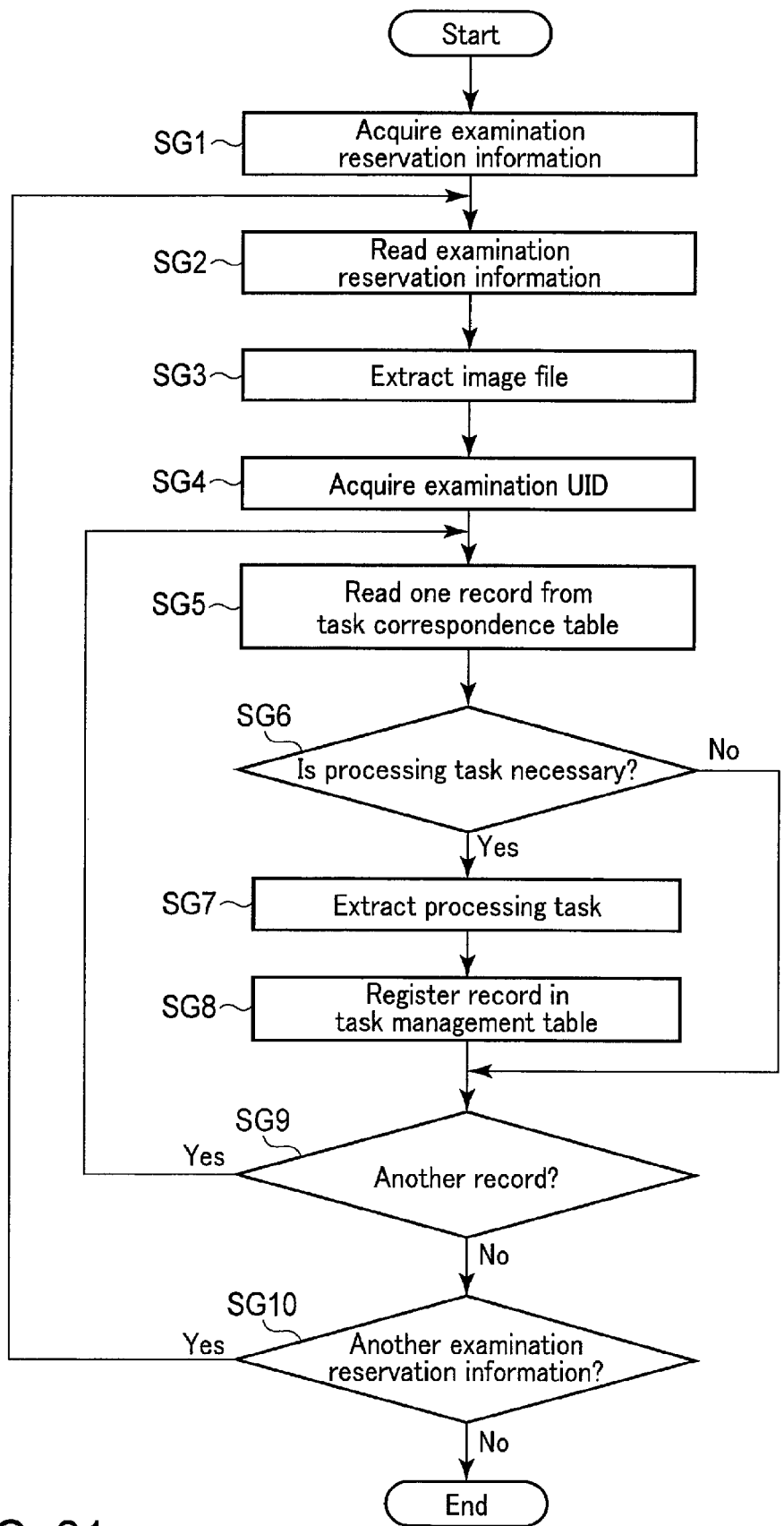
FIG. 21 is a flowchart showing a procedure in which control circuitry according to the modification specifies a processing task.

An operation in which the medical image display apparatus 10B having the above arrangement specifies a processing task will be described in accordance with a processing procedure in the control circuitry 11B shown in FIG. 21. FIG. 21 is a flowchart showing an example of a procedure in which the control circuitry 11B according to the modification specifies a processing task. For the sake of clarity, assume that processing tasks necessary for a requested examination are "MPR" and "large intestine analysis". Assume also that an examination technician has executed "MPR" at the time of imaging examination, but has not been executed "large intestine analysis".

The control circuitry 11B executes the task specifying function 111 upon receiving, via the input interface 13, an activation instruction to activate a predetermined application for displaying a medical image and a capture image. The control circuitry 11B executes the task specifying function 111 to acquire examination reservation information from the RIS server 41 (step SG1).

The control circuitry 11B reads one of the acquired pieces of examination reservation information (step SG2). Assume that in this case, the read examination reservation information contains patient ID "00001", apparatus "X-ray CT examination", procedure "CT colonography", imaging region "large intestine", body posture "none specified", and imaging direction "none specified".

Upon reading examination reservation information, the control circuitry 11B executes the task management function 115B. The control circuitry 11B executes the task management function 115B to read out a medical image file and an SC image file from the image archiving server 30 based on patient ID "00001" contained in the examination reservation information read in step SG2 as a key (step SG3). Additional information in the read medical image file and additional information in the read SC image file each include an examination UID, a series UID, and the like in addition to the patient ID.

The control circuitry 11B acquires an examination UID contained in each of the additional information in the medical image file and the additional information in the SC image file read out from the image archiving server 30 (step SG4).

Upon acquiring an examination UID in step SG4, the control circuitry 11B reads one record from the task correspondence table 151 shown in FIG. 5 (step SG5). The control circuitry 11B reads the first row record, i.e., the record of clinical keyword "CT, large intestine, colonography" and processing task "large intestine analysis", shown in, for example, FIG. 5.

The control circuitry 11B determines whether processing task "large intestine analysis" set in the record read in step SG5 is necessary for the examination reservation information read in step SG2 (step SG6). More specifically, the control circuitry 11B collates apparatus "X-ray CT examination", procedure "CT colonography", imaging region "large intestine", body posture "none specified", and imaging direction "none specified", i.e., the character string contained in the examination reservation information, with clinical keyword "CT, large intestine, colonography" contained in the read record.

Because clinical keyword "CT, large intestine, colonography" is contained in the character string contained in the examination reservation information, the control circuitry 11B determines that the processing task is necessary for the examination reservation information (YES in step SG6). The control circuitry 11B then extracts processing task "large intestine analysis" associated with the clinical keyword from the task correspondence table 151 (step SG7).

The control circuitry 11B registers a record concerning extracted processing task "large intestine analysis" in the task management table 152B shown in FIG. 22 (step SG8). That is, the control circuitry 113 registers the record containing examination UID "0001", processing task "large intestine analysis", and state information "unexecuted" acquired in step SG4 in the task management table 152B.

The control circuitry 11B determines whether the records registered in the task correspondence table 151 include another record for which the necessity to execute a processing task has not been determined (step SG9).

If there is another record for which the necessity to execute a processing task has not been determined (YES in step SG9), the control circuitry 11B reads one record for which the necessity to execute a processing task has not been determined from the task correspondence table 151 (step SG5), and executes the processing in and after step SG6 again.

For example, because the necessity to execute processing task "MPR" shown in FIG. 5 has not been determined, the control circuitry 11B reads out a record containing processing task "MPR" (step SG5). The control circuitry 11B collates clinical keyword "CT" with the character string contained in the examination reservation information (step SG6).

Because the examination reservation information contains clinical keyword "CT", the control circuitry 11B extracts processing task "MPR" from the task correspondence table 151 (step SG7).

As shown in FIG. 22, the control circuitry 11B registers a record concerning extracted processing task "MPR" in the task management table 152B (step SG8). That is, the control circuitry 11B registers a record containing examination UID "0001", processing task "MPR", and state information "unexecuted" in the task management table 152B.

If there is not another record for which the necessity to execute a processing task has not been determined (NO in step SG9), the control circuitry 11B determines whether there is another examination reservation information for which the necessity of a processing task has not been determined (step SG10).

If there is another examination reservation information for which the necessity of a processing task has not been determined (YES in step SG10), the control circuitry 11B reads one piece of examination reservation information (step SG2), and executes the processing from step SG3 to step SG9 again.

If there is not another examination reservation information for which the necessity of a processing task has not been determined (NO in step SG10), the control circuitry 11B finishes processing by the task specifying function 111.

Figure 23:
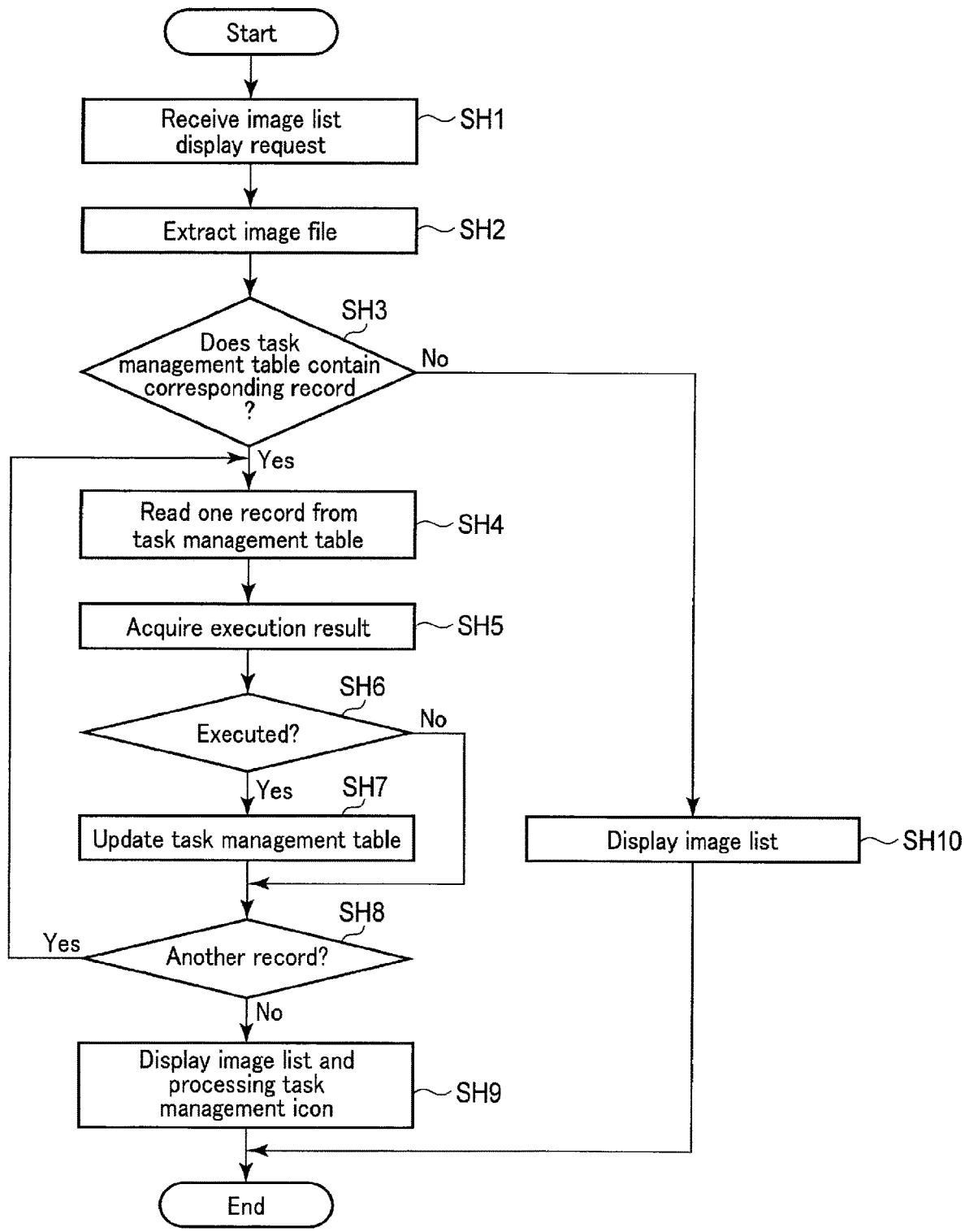
FIG. 23 is a flowchart showing a procedure in which the control circuitry according to the modification determines, in response to an image list display request, whether a processing task has been executed, and displays image data representing the determination result on the display.

The next will describe an operation in which the medical image display apparatus 10B displays state information registered in the task management table 152B on the display 12 in accordance with an image list display request. FIG. 23 is a flowchart showing a procedure in which the control circuitry 11B according to the modification determines, in accordance with an image list display request, whether a processing task has been executed and displays image data representing the determination result on the display 12. Assume that an image list display request is issued by designating, for example, a patient ID and an examination UID.

The control circuitry 11B receives an image list display request via the input interface 13 (step SH1). More specifically, first of all, an interpretation doctor or the like designates a patient as an examination target via the input interface 13.

As shown in FIG. 8, the control circuitry 11B executes the task execution state determination function 112 for the patient indicated by patient ID "00001" upon reception of an image list display request concerning the examination executed "at 7 a.m. on Mar. 4, 2016". The control circuitry 11 executes the task execution state determination function 112 to extract a medical image file and an SC image file containing the examination UID assigned to this examination, for example, "0001", from medical image files and SC image files read out in advance from the image archiving server 30 based on patient ID "00001" as a key (step SH2).

The control circuitry 11B determines whether a task management table 152B contains a record corresponding to examination UID "0001" (step SH3).

Upon determining in step SH3 that the task management table 152B does not include any record corresponding to examination UID "0001" (NO in step SH3), the control circuitry 11B displays an image list concerning the medical image file extracted in step SH2 in the image list display area F3 shown in FIG. 8 (step SH10).

If the task management table 152B contains a record corresponding to examination UID "0001" (YES in step SH3), the control circuitry 11B reads one record corresponding to examination UID "0001" from the task management table 152B (step SH4).

The control circuitry 11B refers to additional information in the SC image file extracted in step SH2 to acquire an execution result of a processing task contained in the record read from the task management table 152B shown in FIG. 22 (step SH5). The control circuitry 11B acquires an execution result of processing task "large intestine analysis" contained in the record corresponding to examination UID "0001" shown in, for example, FIG. 22. More specifically, the control circuitry 11B acquires the number of SC image files, of the SC image files corresponding to examination UID "0001", in each of which information capable of specifying the processing task contained in the corresponding additional information represents processing task "large intestine analysis".

The control circuitry 11B compares the number of SC image files acquired in step SH5 with a number set in advance for each processing task to determine whether the corresponding processing task has been executed (step SH6). More specifically, the control circuitry 11B determines whether processing task "large intestine analysis" has been executed by comparing the number of SC image files, of the SC image files corresponding to examination UID "0001", in each of which information capable of specifying the processing task contained in the corresponding additional information represents processing task "large intestine analysis" with a number set in advance for processing task "large intestine analysis".

If the SC image files corresponding to examination UID "0001" do not include any SC image file in which information capable of specifying the processing task contained in the corresponding additional information represents processing task "large intestine analysis", the control circuitry 11B determines that processing task "large intestine analysis" has not been executed (NO in step SH6). The control circuitry 11B then determines whether the records corresponding to examination UID "0001" in the task management table 152B include another record for which whether a processing task has been executed has not been determined (step SH8).

If the records corresponding to examination UID "0001" in the task management table 152B include another record for which whether a processing task has been executed has not been determined (YES in step SH8), the control circuitry 11B reads one record from the task management table 152 (step SH4), and executes the processing in and after step SH5 again. The control circuitry 11B executes the processing in and after step SH4 again because the records corresponding to examination UID "0001" in the task management table 152B include another record for which whether the processing task has been executed has not been determined, i.e., a record corresponding to examination UID "0001" and processing task "MPR", as shown in FIG. 22.

More specifically, the control circuitry 11B acquires the number of SC image files, of the SC image files corresponding to examination UID "0001", in each of which information capable of specifying the processing task contained in the corresponding additional information represents processing task "MPR" (step SH5).

The control circuitry 11B determines whether processing task "MPR" has been executed by comparing the number of SC image files, of the SC image files corresponding to examination UDI "0001", in each of which information capable of specifying the processing task contained in the corresponding additional information represents processing task "MPR" with a number set in advance for processing task "MPR" (step SH6).

If the number of SC image files, of the SC image files corresponding to examination UID "0001", in each of which information capable of specifying the processing task contained in the corresponding additional information represents processing task "MPR" is equal to a number set in advance, the control circuitry 11B determines that the state information of processing task "large intestine analysis" is "executed" (YES in step SH6). The control circuitry 11B then updates the value of the state information of the record corresponding to examination UID "0001" and processing task "MPR" from "unexecuted" shown in FIG. 22 to "executed" shown in FIG. 24 in the task management table 152B.

The control circuitry 11B executes the display control function 113 if the records corresponding to examination UID "0001" in the task management table 152B include no other record for which whether a processing task has been executed has not been determined (NO in step SH8). The control circuitry 11B executes the display control function 113 to refer to the task management table 152B shown in FIG. 24 so as to generate, for, for example, each series, image data representing whether a processing task corresponding to examination UID "0001" assigned to the examination designated in an image list display request has been executed, in accordance with the value of the state information of the processing task.

The control circuitry 11B controls the display 12 to display the generated image data as an image processing state display icon in the image list display area F3 shown in FIG. 8 together with an image list concerning the medical image file (step SH9). The image processing state display icon is an icon capable of identifying whether the processing task corresponding to a predetermined order number has been executed. Assume that in the modification, the image processing state display icon shown in FIG. 10 is generated in accordance with the value of the state information of a record extracted based on examination UID "0001" as a key assigned to the examination designated in an image list display request.

Figure 25:
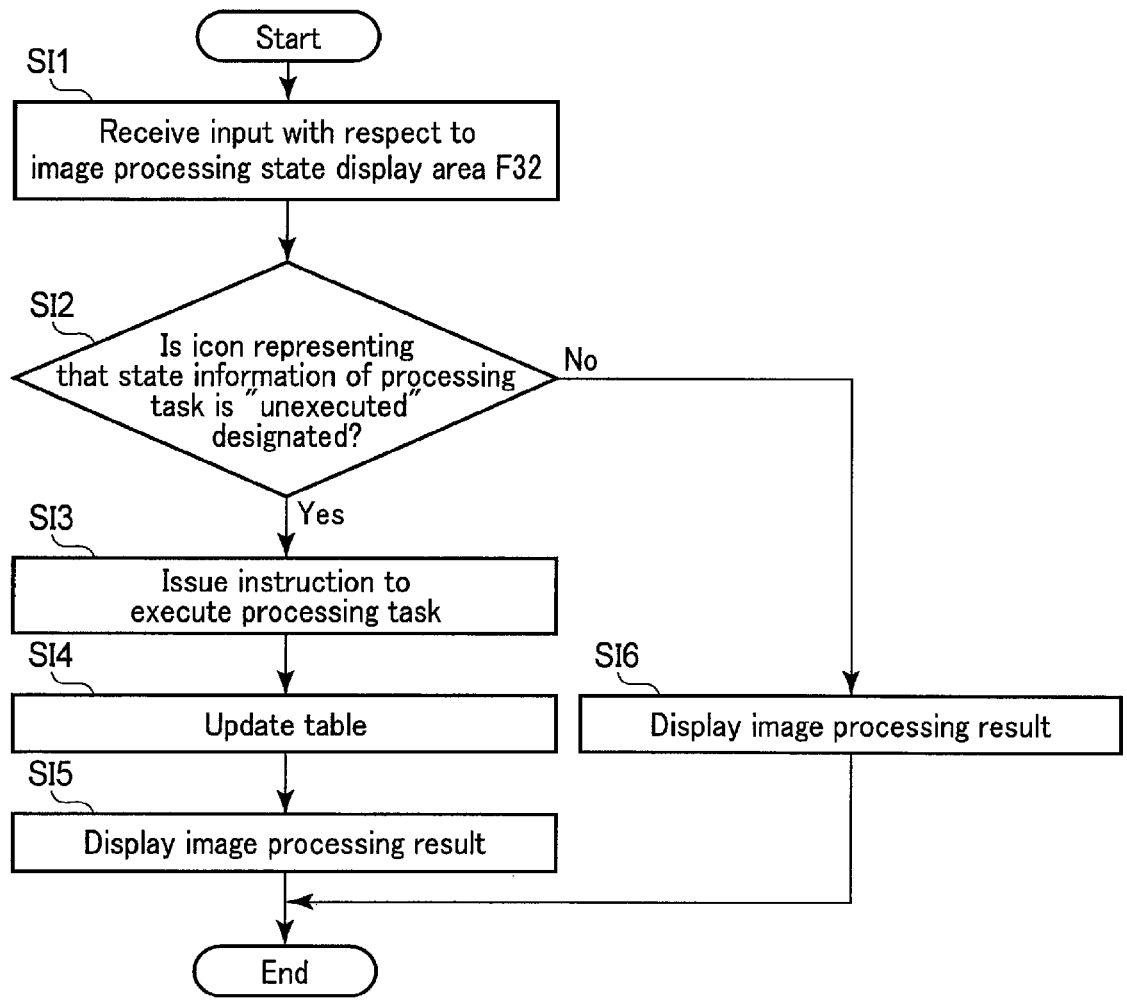
FIG. 25 is a flowchart showing a procedure for processing to be performed upon designation of a predetermined image processing state display icon displayed on the display according to the modification.

A procedure for executing a processing task upon designation of an image processing state display icon displayed on the display 12 according to the modification will be described next with reference to FIGS. 10 and 25. FIG. 25 is a flowchart showing an example of a procedure for processing to be performed when a predetermined image processing state display icon displayed on the display 12 according to the modification is designated.

First of all, the control circuitry 11B stands by until an arbitrary position in the image processing state display area F32 shown in FIG. 11 is touched via the input interface 13 (step SI1).

When an arbitrary position in the image processing state display area F32 is touched, the control circuitry 11B determines whether the touched position is a position corresponding to an image processing state display icon representing that the corresponding processing task has not been executed (step SI2).

The control circuitry 11B executes the task execution instruction function 114 (step SI3) if the touched position on the image processing state display area F32 is a position corresponding to the image processing state display icon representing that the processing task has not been executed (YES in step SI2). The control circuitry 11B executes the task execution instruction function 114 to generate execution instruction information for issuing an instruction to execute the processing task associated with the image processing state display icon. The control circuitry 11B transmits the generated execution instruction information to, for example, the workstation 20 via the communication interface 14.

When, for example, the image processing state display icon I5 shown in FIG. 10 is designated, the control circuitry 11B transfers an instruction to execute processing task "large intestine analysis" to the workstation 20 via the communication interface 14. With this operation, the control circuitry 23 of the workstation 20 generates a capture image by executing processing task "large intestine analysis".

The workstation 20 generates an SC image file by converting the generated capture image into a format complying with, for example, the DICOM standard. The workstation 20 then transmits an execution result containing information indicating "executed" to the medical image display apparatus 10B via the communication interface 21. The workstation 20 transmits the generated SC image file to the image archiving server 30.

Upon receiving the execution result containing information indicating "executed" from the workstation 20, the medical image display apparatus 10B acquires the SC image file transmitted from the workstation 20 to the image archiving server 30 from the image archiving server 30.

Upon acquiring an SC image file generated as a result of executing the processing task for which an execution instruction has been issued from the image archiving server 30, the control circuitry 11B executes the task management function 115B to update the state information of the processing task to "executed" in the task management table 152B (step SI4). For example, the control circuitry 11B updates the state information of processing task "large intestine analysis" from "unexecuted" to "executed".

The control circuitry 11B executes the display control function 113 upon updating the state information of the processing task to "executed" in the task management table 152B. The control circuitry 11B executes the display control function 113 to refer to the task management table 152B so as generate image data representing that the state information of processing task "large intestine analysis" is "executed". The control circuitry 11B controls the display 12 to display the generated image data as an image processing state display icon in the image list display area F3 shown in, for example, FIG. 10 together with an image list concerning the medical image file (step SI5).

The control circuitry 11B executes the display control function 113 (step SI6) if a touched position on the image processing state display area F3 is not a position corresponding to an image processing state display icon representing that the processing task has not been executed, that is, is a position corresponding to an image processing state display icon representing that a predetermined processing task has been executed (NO in step SI2). The control circuitry 11B executes the display control function 113 to, for example, display a capture image as a result of executing a processing task. When, for example, the image processing state display icon I4 shown in FIG. 10 is designated, the control circuitry 11B displays an MPR image as a result of executing processing task "MPR".

According to the modification, the control circuitry 11B extracts a medical image file and an SC image file based on an examination UID as a key instead of an order number. This makes it possible to easily manage processing tasks by using the examination UID contained in each of pieces of additional information in medical image files and SC image files complying with, for example, the DICOM standard.

Other Embodiments

Note that the present invention is not limited to the above embodiments. For example, in the above embodiments, the state information of a processing task is displayed in an icon form. However, this state information may be displayed in the form of an image file representing an execution result of a processing task in characters or may be displayed in a form with which an image processing program is associated.

In the first embodiment, the control circuitry 23 of the workstation 20 executes a processing task. However, this is not exhaustive. That is, the control circuitry 11 of the medical image display apparatus 10 may be equipped with the same function as the task execution function 231, and the medical image display apparatus 10 may execute processing tasks.

The second embodiment includes the viewer 10A and the image archiving server 30A as different housings. However, this is not exhaustive. That is, the image archiving server 30A may incorporate the input interface 13A and the display 12A of the viewer 10A and may be used as a medical image display apparatus. In this case, the image archiving server 30A receives an image list display request via the input interface 13A, and implements display of an image processing state display icon and the like via the display 12A.

In the above embodiment, the values that state information in the task management table 152 can assume are not limited to "executed" and "unexecuted". For example, the values that state information can assume include "partially executed". Note that "partially executed" is a value that can be assumed when, for example, there are a plurality of processing tasks associated with image processing state display icons, and only some of the processing tasks have been executed. That is, "partially executed" is a value that can be assumed when only some of SC image files and the like set in advance for each processing task are actually generated.

In this case, in an image processing state display icon indicating that state information is "partially executed", an image that allows recognition of state information as "partially executed", for example, a character string representing "partially executed", is displayed. When an image processing state display icon representing that state information is "partially executed" is designated, the control circuitry 11 according to the first embodiment controls the display 12 to parallelly display an icon with which an execution result of a processing task is associated and an icon with which a program for generating an instruction to execute a predetermined processing task that has not been executed is associated.

In the above embodiments, the task execution state determination function 112 determines whether a processing task has been executed. However, this is not exhaustive. That is, an application for each processing task may be implemented to determine whether the processing task has been executed.

The term "processor" used in the above description means, for example, a CPU (Central Processing Unit), a GPU (Graphics Processing Unit), or circuitry such as an ASIC (Application Specific Integrated Circuit), or a programmable logic device (for example, SPLD (Simple Programmable Logic Device), CPLD (Complex Programmable Logic Device), or FPGA (Field Programmable Logic Device)). The function of a processor is implemented by reading out and executing a program stored in a memory. Note that a program may be directly incorporated in the circuitry of a processor instead of being stored in a memory. In this case, the function of a processor is implemented by reading out and executing a program incorporated in circuitry. Note that each processor according to each embodiment described above may be formed as a single processor to implement its function by combining a plurality of independent circuits in addition of being formed as single circuitry for each processor. In addition, a plurality of constituent elements in FIGS. 2 and 3 may be integrated into a single processor to implement its function. Furthermore, a plurality of constituent elements in FIGS. 13 and 14 may be integrated into a single processor to implement its function.

Some embodiments of the present invention have been described above. However, these embodiments are presented merely as examples and are not intended to restrict the scope of the invention. These novel embodiments can be carried out in various other forms, and various omissions, replacements, and alterations can be made without departing from the spirit of the invention. The embodiments and their modifications are also incorporated in the scope and the spirit of the invention as well as in the invention described in the claims and their equivalents.

The invention claimed is:

1. A medical image display apparatus comprising:
a memory configured to store a task management table associating a processing task executed for a medical image with state information representing whether or not the processing task has been executed; and
processing circuitry configured to
extract, from the task management table, state information that is associated with a processing task for a medical image requested to be displayed,
display, based on the extracted state information, side by side, information indicative of whether or not a processing task has been executed for the requested medical image, and the medical image; and
display, responsive to extracting the state information representing that the processing task has not been executed, an icon which is indicative that a processing task has not been executed for the requested medical image and through which executing the processing task can be instructed.

2. The medical image display apparatus according to claim 1, wherein the processing circuitry is configured to display, responsive to extracting the state information representing that the processing task has been executed, an other icon which is indicative that a processing task has been executed for the requested medical image and through which displaying a medical image generated by executing the processing task can be instructed.

3. The medical image display apparatus according to claim 2, wherein the processing circuitry is configured to include, in the other icon, the medical image generated by executing the processing task in a reduced size.

4. The medical image display apparatus according to claim 1, wherein the processing circuitry is configured to execute, responsive to the instruction for executing the processing task through the icon, the processing task for the instructed medical image and to update, upon executing the instructed processing task, the state information associated with the processing task in the task management table.

5. The medical image display apparatus according to claim 1, wherein the processing circuitry is configured to start executing the processing task in accordance with designation of the icon and update the state information associated with the processing task in the task management table upon completion of the processing task.

6. The medical image display apparatus according to claim 1, wherein the processing circuitry is configured to determine whether or not the processing task has been executed based on presence or absence of a medical image corresponding to the processing task.

7. The medical image display apparatus according to claim 1, wherein the processing circuitry is configured to specify a processing task corresponding to examination reservation information and register the specified processing task and state information representing whether or not the processing task corresponding to the examination reservation information has been executed in the task management table in association with each other.

8. The medical image display apparatus according to claim 1, wherein the processing circuitry is configured to start executing the processing task in accordance with designation of the icon and display an identifier indicative that the processing task is being executed.

9. A medical image management system including an image archiving server configured to archive a medical image, and a medical image display apparatus configured to display the medical image, the medical image display apparatus comprising:
a memory configured to store a task management table associating a processing task executed for a medical image with state information representing whether or not the processing task has been executed; and
processing circuitry configured to
extract, from the task management table, state information that is associated with a processing task for a medical image requested to be displayed,
display, based on the extracted state information, side by side, information indicative of whether or not a processing task has been executed for the requested medical image, and the medical image; and
display, responsive to extracting the state information representing that the processing task has not been executed, an icon which is indicative that a processing task has not been executed for the requested medical image and through which
executing the processing task can be instructed.

10. A medical image management system including an image archiving server configured to archive a medical image and a viewer configured to display the medical image,
the image archiving server comprising:
a memory configured to store a task management table associating a processing task executed for a medical image with state information representing whether or not the processing task has been executed; and
processing circuitry configured to
extract, from the task management table, state information that is associated with a processing task for a medical image requested to be displayed,
display, based on the extracted state information, side by side, information indicative of whether or not a processing task has been executed for the requested medical image, and the medical image; and
display, responsive to extracting the state information representing that the processing task has not been executed, an icon which is indicative that a processing task has not been executed for the requested medical image and through which executing the processing task can be instructed.

11. The medical image display apparatus according to claim 2, wherein, when the other icon is designated, the processing circuitry is configured to display a medical image as a result of executing the processing task.

* * * * *